United States Patent
Childress

(10) Patent No.: US 12,076,452 B2
(45) Date of Patent: Sep. 3, 2024

(54) MODULATED ULTRAVIOLET LIGHT SANITIZING SYSTEM AND METHOD

(71) Applicant: THE BOEING COMPANY, Chicago, IL (US)

(72) Inventor: Jamie J. Childress, Mercer Island, WA (US)

(73) Assignee: The Boeing Company, Chicago, IL (US)

( * ) Notice: Subject to any disclaimer, the term of this patent is extended or adjusted under 35 U.S.C. 154(b) by 732 days.

(21) Appl. No.: 17/336,595

(22) Filed: Jun. 2, 2021

(65) Prior Publication Data

US 2022/0111086 A1    Apr. 14, 2022

Related U.S. Application Data

(60) Provisional application No. 63/118,303, filed on Nov. 25, 2020, provisional application No. 63/091,444, filed on Oct. 14, 2020.

(51) Int. Cl.
*A61L 2/10* (2006.01)
*A61L 2/24* (2006.01)
*A61L 2/26* (2006.01)

(52) U.S. Cl.
CPC ...... *A61L 2/10* (2013.01); *A61L 2/24* (2013.01); *A61L 2/26* (2013.01); *A61L 2202/11* (2013.01); *A61L 2202/14* (2013.01); *A61L 2202/25* (2013.01)

(58) Field of Classification Search
CPC ..... A61L 2/10; A61L 2/24; A61L 2/26; A61L 9/20; A61L 9/205; A61L 2202/11; A61L 2202/14; A61L 2202/25; A61L 2209/11; A61L 2209/111; A61L 2209/12

See application file for complete search history.

(56) References Cited

U.S. PATENT DOCUMENTS

| | | |
|---|---|---|
| 11,382,993 B2 | 7/2022 | Childress |
| 11,617,810 B2 | 4/2023 | Brockschmidt, Jr. et al. |
| 11,679,169 B2 | 6/2023 | Brockschmidt, Jr. et al. |

(Continued)

FOREIGN PATENT DOCUMENTS

| | | |
|---|---|---|
| KR | 20130125436 | 11/2013 |
| KR | 20200054640 | 5/2020 |

OTHER PUBLICATIONS

Extended European Search Report for EP 21210200.8-1012, dated May 9, 2022.

(Continued)

*Primary Examiner* — Timothy C Cleveland
(74) *Attorney, Agent, or Firm* — Joseph M. Butscher; The Small Patent Law Group LLC

(57) ABSTRACT

A system and method for sanitizing a target space include an ultraviolet (UV) lamp, an occupancy sensor, and a control unit operably connected to the occupancy sensor and the UV lamp. The UV lamp is configured to emit UV light into the target space. The occupancy sensor is configured to monitor the target space and generate sensor signals indicative of an occupancy of the target space by at least one person. The control unit is configured to receive the sensor signals generated by the occupancy sensor and to modulate an irradiance of the UV light emitted by the UV lamp over time based on the occupancy of the target space.

31 Claims, 25 Drawing Sheets

(56) References Cited

U.S. PATENT DOCUMENTS

| | | |
|---|---|---|
| 11,782,197 B2 | 10/2023 | Gross |
| 11,793,896 B2 | 10/2023 | Brockschmidt, Jr. et al. |
| 11,957,810 B2 | 4/2024 | Callahan et al. |
| 2020/0215214 A1* | 7/2020 | Rosen .................... A61L 2/084 |
| 2021/0018884 A1* | 1/2021 | Kupa ................... H05B 47/115 |
| 2021/0299290 A1* | 9/2021 | Maxik .................... F21S 8/026 |
| 2021/0346540 A1 | 11/2021 | Childress et al. |
| 2021/0346541 A1 | 11/2021 | Callahan et al. |
| 2021/0386883 A1 | 12/2021 | Childress |
| 2022/0023459 A1 | 1/2022 | Colletti et al. |
| 2022/0023478 A1 | 1/2022 | Childress |

OTHER PUBLICATIONS

U.S. Appl. No. 29/735,235, filed May 19, 2020.
"Honeywell UV Treatment System," https://aerospace.honeywell.com/en/learn/products/cabin/uv-cabin-system.

* cited by examiner

MODULATED ULTRAVIOLET LIGHT SANITIZING SYSTEM AND METHOD

RELATED APPLICATIONS

This application relates to and claims priority benefits from U.S. Provisional Patent Application No. 63/118,303, entitled "Modulated Ultraviolet Light Sanitizing System and Method," filed Nov. 25, 2020, which is hereby incorporated by reference in its entirety.

This application also relates to U.S. Provisional Patent Application No. 63/091,444, entitled "Ultraviolet Light Sanitizing Systems and Methods," filed Oct. 14, 2020, which is hereby incorporated by reference in its entirety.

FIELD OF THE DISCLOSURE

Embodiments of the present disclosure generally relate to ultraviolet (UV) light sanitizing systems, such as may be used to sanitize structures and areas within vehicles, and more particularly to systems and methods for modulating the irradiance of the emitted UV light based on occupancy.

BACKGROUND OF THE DISCLOSURE

Vehicles such as commercial aircraft are used to transport passengers between various locations. Systems are currently being developed to disinfect or otherwise sanitize surfaces within aircraft, for example, that use ultraviolet (UV) light.

A UV light sanitizing system typically includes a UV lamp that includes one or more UV light emitters. When a UV light sanitizing system is installed within a public space, people may periodically enter and occupy the space. Certain rooms that have installed UV light sanitizing systems are configured to immediately deactivate the UV lamp upon detection of one or more persons within the room to preclude the one or more persons from receiving a dose of UV light. Even if the occupancy of the room is transient, the UV lamp is automatically controlled to stop emitting UV light, or to reduce the power output of the UV light to a very low, nominal level. In rooms or spaces that are periodically occupied, such drastic responses to occupation may interfere with the disinfection of the components within the rooms or spaces by reducing the UV dose administered to the components and extending the time required to reach a certain predetermined UV dose.

UV light sanitizing systems draw electrical energy from a power source to power the UV lamp. When the UV light sanitizing system is powered by a power source that has a limited amount of available electrical energy, such as a battery pack within a vehicle, consumption of the available electrical energy by the UV light sanitizing system can deplete the power source, which limits the amount of time that the UV lamp can be operated, the irradiance of UV light emitted by the UV lamp, and/or the electrical energy that can be supplied to other loads, such as other electrical devices, before having to replace or recharge the power source. For example, when the UV lamp draws power, it may be difficult to budget the power to allow for the proper functioning of all desired systems during a common time period. In the case of a battery that is local and integrated within the UV light sanitizing system, there may be a predefined amount of electrical energy available. There is a benefit to reduce energy usage to increase the duration and/or efficiency of UV lamp operation per charge cycle. Even if the power source has abundant electrical energy available to power the UV lamp, energy costs may be proportional to energy usage, so excessive power consumption may unduly increase the energy cost.

SUMMARY OF THE DISCLOSURE

A need exists for a system and a method for dynamic disinfection of periodically occupied rooms and spaces, where the irradiance of the UV light is modulated based on the occupancy of the rooms and spaces. For example, the irradiance may be modified in response to persistent occupation of a room, but not modified in response to transient occupation of the room.

With that need in mind, certain embodiments of the present disclosure provide a sanitizing system for modulating irradiance of UV light emitted by a UV lamp. The sanitizing system includes an ultraviolet (UV) lamp, an occupancy sensor, and a control unit operably connected (e.g., communicatively connected) to the occupancy sensor and the UV lamp. The UV lamp is configured to emit UV light into a target space. The occupancy sensor is configured to monitor the target space and generate sensor signals indicative of an occupancy of the target space by at least one person. The control unit, which includes one or more processors, is configured to receive the sensor signals generated by the occupancy sensor and to modulate an irradiance of the UV light emitted by the UV lamp over time based on the occupancy of the target space.

Certain embodiments of the present disclosure provide a method for sanitizing a target space. The method includes emitting ultraviolet (UV) light into a target space, and monitoring the target space via one or more occupancy sensors. The one or more occupancy sensors are configured to generate sensor signals indicative of an occupancy of the target space by at least one person. The method also includes analyzing the sensor signals via a control unit comprising one or more processors, and modulating, via the control unit, an irradiance of the UV light emitted into the target space over time based on the occupancy of the target space.

Certain embodiments of the present disclosure provide a sanitizing system disposed onboard a vehicle. The sanitizing system includes a first ultraviolet (UV) system, a second UV system, and a control unit that comprises one or more processors and is operably connected to the first and second UV systems. The first UV system includes a first lamp subset of one or more UV lamps and a first sensor subset of one or more occupancy sensors. The first lamp subset is configured to emit UV light into a first target space within the vehicle, and the first sensor subset is configured to generate first sensor signals indicative of an occupancy of the first target space by at least one person. The second UV system includes a second lamp subset of one or more UV lamps and a second sensor subset of one or more occupancy sensors. The second lamp subset is configured to emit UV light into a second target space within the vehicle, and the second sensor subset is configured to generate second sensor signals indicative of an occupancy of the second target space by at least one person. The control unit is configured to (i) receive the first sensor signals generated by the first sensor subset and the second sensor signals generated by the second sensor subset, (ii) modulate an irradiance of the UV light emitted by the first lamp subset over time based on the occupancy of the first target space, and (iii) modulate an irradiance of the UV light emitted by the second lamp subset over time based on the occupancy of the second target space.

DETAILED DESCRIPTION OF THE DISCLOSURE

Figure 1:
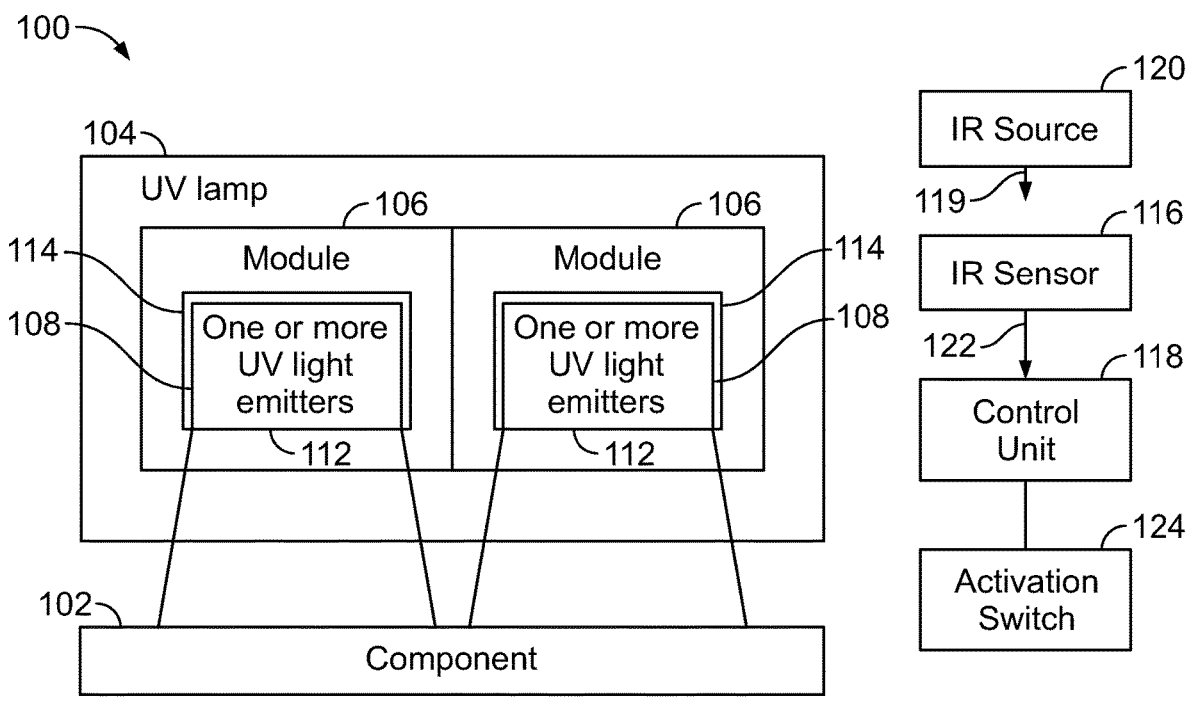
FIG. 1 illustrates a schematic block diagram of a system for disinfecting a component, according to an embodiment of the present disclosure.

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular condition can include additional elements not having that condition.

Certain embodiments of the present disclosure provide a system for sanitizing (for example, disinfecting, decontaminating, cleaning, or the like) one or more components within a target space. The system includes at least a UV lamp, a sensor (also referred to herein as an occupancy sensor), and a control unit having one or more processors. The system is configured such that the irradiance of the UV light emitted by the UV lamp is modulated based on the occupancy of the space. The occupancy of the space refers to both the initial detection of the presence of at least one person within the space as well as the persistence of the detected presence of the at least one person. In one or more embodiments, the occupancy may also refer to an expected or predicted presence of at least one person within the space, such as based on historical data, regardless of whether or not at least one person is actually detected in the space. The irradiance of the UV light generally refers to a power output of the UV light, and more specifically refers to the radiant flux (e.g., power) received by a surface per unit area, which can be measured in units of milliwatt per square centimeter (mW/$cm^2$). In one or more embodiments, the irradiance is modulated such that the UV light has a full irradiance level, to provide a high disinfection dose to one or more components in a target space, when the target space is unoccupied. The system modulates the UV light by reducing and varying the irradiance of the UV light in response to periodic occupation of the target space by one or more people. For example, the system may gradually reduce the irradiance level of the UV light, in discrete steps or in a continuous slide, during a period of persistent occupation of the target space. Eventually, the system may deactivate the UV lamp to stop emitting UV light or may continuously emit UV light at a low irradiance level that is safe for human tissues at extended periods of exposure.

In one or more embodiments, the control unit may include prediction module or feature that utilizes data analysis, machine learning, and/or artificial intelligence (AI). The prediction module may analyze historical data representing the occupancy of the target space over time to "learn" and generate occupancy trends. The occupancy trends may indicate the frequency that people pass through the space over an extended period of time, such as a day, a week, a month, a year, or the like. The prediction module may use the occupancy trends to predict upcoming occupancy cycles or periods prior to actual detection by the occupancy sensor. The control unit may adjust the irradiance of the UV light based on the predicted upcoming occupancy cycles to reach a balance between providing sufficient UV dosage for disinfection without risking harm to people within the space.

In certain embodiments, the UV lamp has one or more UV light emitters and optionally may include one or more wavelength selective filters. The UV lamp may be an excimer lamp. The UV light emitters may be light emitting diodes (LEDs), bulbs, and/or the like, that emit UV light in a far UV light spectrum and/or a UV-C spectrum. The far UV light spectrum includes the wavelength 222 nm, which neutralizes (such as kills) microbes (for example, viruses and bacteria), while posing no risk to humans. The UV-C spectrum includes the wavelength 254 nm. The UV lamp may be used within an enclosed room to decontaminate and kill pathogens. The enclosed room may be within an internal cabin of a vehicle, such as a passenger cabin, galley, and/or lavatory of a commercial aircraft. In an embodiment, the sanitizing system is a fixed system such that the UV lamp and the occupancy sensor are fixedly secured in place within the room. Optionally, one or more components of the sanitizing system may be portable. For example, the UV lamp may be mounted on a cart or robot that moves relative to the room to disinfect components within the room. For example, operating the UV lamp to emit sanitizing UV light having a wavelength within the far UV spectrum or UVC spectrum may be used with a portable system or a fixed system.

FIG. 1 illustrates a schematic block diagram of a system 100 for disinfecting a component 102, according to an embodiment of the present disclosure. The component 102 can be any structure that is to be disinfected with UV light. For example, the component 102 can be a structure within a vehicle, a fixed building, or the like. As example, the component 102 can be a passenger seat within a vehicle, a portion of a lavatory (such as a toilet, sink, door handle, and/or the like), a counter or other such surface within a kitchen or galley, and/or the like.

The system 100 includes a UV lamp 104 that includes a plurality of modules 106 coupled together. For example, the UV lamp 104 includes a first module 106 coupled to a second module 106. Optionally, the UV lamp 104 can include more than two modules 106.

Each module 106 includes one or more UV light emitters 108 that are configured to emit UV light through an aperture 112. The UV light emitters 108 can emit UV light within the far UV spectrum, such as from 200 nanometers (nm) to 230 nm, and/or within the UV-C spectrum, such as from 230 nm to 280 nm. For example, the UV light emitters can emit UV light at 222 nm. As another example, the UV light emitters 108 can emit UV light at 254 nm. In at least one embodiment, the UV light emitters 108 of the modules 106 emit UV light at the same wavelength. In at least one other embodiment, the UV light emitters 108 of the modules 106 emit UV light at different wavelengths. For example, the UV light emitters 108 of a first module 106 emit UV light within the far UV spectrum, and the UV light emitters 108 of a second module 106 emit UV light within the UV-C spectrum, or vice versa.

The modules 106 are coupled together to form the light emitting portion of the UV lamp 104. The modules 106 can be removably coupled together. As such, the UV lamp 104 provides a modular assembly that can be customized to a desired size, shape, and lighting capability. Further, if a module 106 is in need of repair, the module 106 can be removed from the UV lamp 104 and replaced within another module 106. Accordingly, the modules 106 allow for efficient production and maintenance of the UV lamp 104.

In at least one embodiment, portions of the modules 106 are covered with one or more electromagnetic interference (EMI) shields 114. For example, in at least one embodiment, the one or more UV light emitters 108 are surrounded on one or more surfaces with an EMI shield 114, with the aperture 112 being uncovered by the EMI shield 114. In at least one embodiment, the EMI shield 114 is a metal cover, such as a foil formed of aluminum, steel, or the like that covers a housing of the module 106 with the aperture 112 remaining uncovered. Optionally, the modules 106 do not include the EMI shield 114.

The UV lamp 104 can be a fixture within a room or area. For example, the UV lamp 104 can be secured within a lavatory, galley, kitchen, or various other areas. The UV lamp 104 can be fixed in position within the area. Optionally, the UV lamp 104 can be movable between a stowed position and a deployed position within the area. In at least one other embodiment, the UV lamp 104 can be removably securable to various structures, such as securing mounts located within an area, such as within a vehicle.

In at least one embodiment, the system 100 also includes an infrared (IR) sensor 116 in communication with a control unit 118, such as through one or more wired or wireless connections. The control unit 118 is also in communication with the UV light emitters 108 of the modules 106, such as through one or more wired or wireless connections. In at least one embodiment, the UV lamp 104 includes the IR sensor 116 and/or the control unit 118. Optionally, the IR sensor 116 and/or the control unit 118 can be remotely located from the UV lamp 104.

In operation, the control unit 118 selectively activates and deactivates the UV light emitters 108 based on an IR signal emitted by and received from the IR sensor 116. For example, the IR sensor 116 is configured to receive an IR light signal 119 emitted by an IR source 120, either directly from the IR source 120, or indirectly from a reflector that receives and reflects the IR light signal 119 from the IR source 120. When the IR sensor 116 receives the IR light signal 119, the IR sensor 116 outputs a sensed IR signal 122 to the control unit 118. Based on the received sensed IR signal 122, the control unit 118 activates the one or more UV light emitters 108 to emit the UV light. If, however, the IR sensors 116 does not receive the IR light signal 119 (such as if the IR light signal 119 is blocked by an individual), the IR sensor does not output the sensed IR signal 122 to the control unit 118. In response to not receiving the sensed IR signal 122, the control unit 118 deactivates the UV light emitters 108 so that they do not emit the UV light.

In at least one embodiment, an activation switch 124 is in communication with the control unit 118, such as through one or more wired or wireless connections. The activation switch 124 can be secured to the UV lamp 104. That is, the UV lamp 104 can include the activation switch 124. Optionally, the activation switch 124 can be remotely located from the UV lamp 104. When the activation switch 124 is engaged to activate the UV light emitters 108, the control unit 118 operates as explained above (that is, the control unit 118 selectively activates and deactivates the UV light emitters based on the signal received from the IR sensor 116). When the activation switch 124 is disengaged so that the UV light emitters 108 are not to emit the UV light, the control unit 118 maintains the UV light emitters 108 in a deactivated state even if the sensed IR signal 122 is received from the IR sensor 116. Optionally, the system 100 may not include the activation switch.

In at least one embodiment, the system 100 includes the UV lamp 104 having UV light emitters 108 whether or not within the modules 106. For example, the UV lamp 104 can be a single, non-modular assembly that is in communication with the control unit 118, which selectively activates and deactivates the UV light emitters 108 as described herein. In at least one other embodiment, the system 100 does not include the IR sensor 116 or the IR source 120.

As used herein, the term "control unit," "central processing unit," "CPU," "computer," or the like may include any processor-based or microprocessor-based system including systems using microcontrollers, reduced instruction set computers (RISC), application specific integrated circuits (ASICs), logic circuits, and any other circuit or processor including hardware, software, or a combination thereof capable of executing the functions described herein. Such are exemplary only, and are thus not intended to limit in any way the definition and/or meaning of such terms. For example, the control unit 118 (and the control unit 604 shown in FIG. 36) may be or include one or more processors that are configured to control operation, as described herein.

The control unit 118 and the control unit 604 are configured to execute a set of instructions that are stored in one or more data storage units or elements (such as one or more memories), in order to process data. For example, the control unit 118 and the control unit 604 may include or be coupled to one or more memories. The data storage units may also store data or other information as desired or needed. The data storage units may be in the form of an information source or a physical memory element within a processing machine.

The set of instructions may include various commands that instruct the control unit 118 and the control unit 604 as a processing machine to perform specific operations such as the methods and processes of the various embodiments of the subject matter described herein. The set of instructions may be in the form of a software program. The software may be in various forms such as system software or application software. Further, the software may be in the form of a collection of separate programs, a program subset within a larger program, or a portion of a program. The software may also include modular programming in the form of object-oriented programming. The processing of input data by the processing machine may be in response to user commands, or in response to results of previous processing, or in response to a request made by another processing machine.

The diagrams of embodiments herein may illustrate one or more control or processing units, such as the control unit 118 and the control unit 604. It is to be understood that the processing or control units may represent circuits, circuitry, or portions thereof that may be implemented as hardware with associated instructions (e.g., software stored on a tangible and non-transitory computer readable storage medium, such as a computer hard drive, ROM, RAM, or the like) that perform the operations described herein. The hardware may include state machine circuitry hardwired to perform the functions described herein. Optionally, the hardware may include electronic circuits that include and/or are connected to one or more logic-based devices, such as microprocessors, processors, controllers, or the like. Optionally, the control unit 118 and the control unit 604 may represent processing circuitry such as one or more of a field programmable gate array (FPGA), application specific integrated circuit (ASIC), microprocessor(s), and/or the like. The circuits in various embodiments may be configured to execute one or more algorithms to perform functions described herein. The one or more algorithms may include aspects of embodiments disclosed herein, whether or not expressly identified in a flowchart or a method.

As used herein, the terms "software" and "firmware" are interchangeable, and include any computer program stored in a data storage unit (for example, one or more memories) for execution by a computer, including RAM memory, ROM memory, EPROM memory, EEPROM memory, and non-volatile RAM (NVRAM) memory. The above data storage unit types are exemplary only, and are thus not limiting as to the types of memory usable for storage of a computer program.

Although the UV lamp 104 in FIG. 1 is shown to include two modules 106 that each include one or more light emitters 108, various embodiments described herein are not limited to the specific makeup of the UV lamp 104 shown in FIG. 1. For example, in one or more embodiments, the UV lamp 104 may have a single module 106 and/or a single UV light emitter 108.

Figure 2:
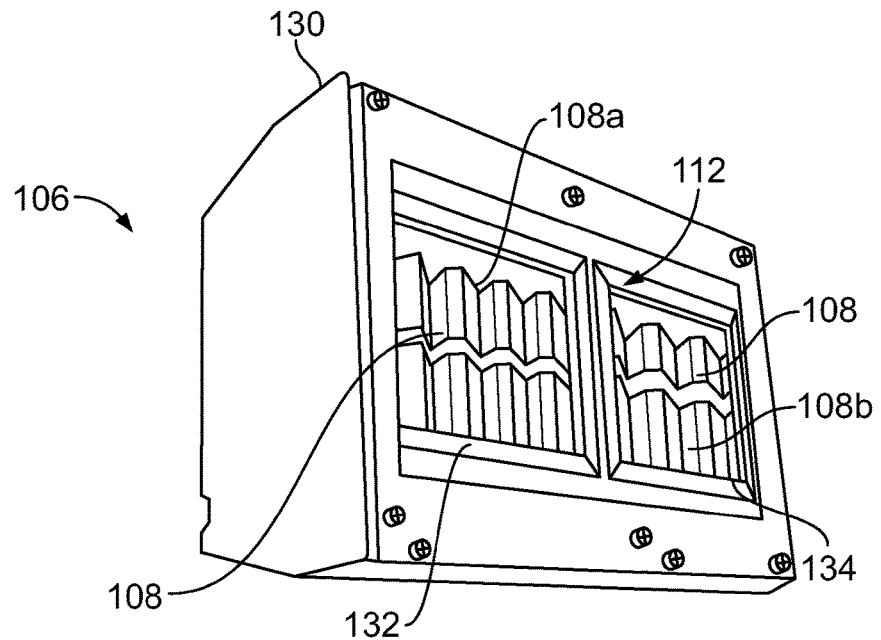
FIG. 2 illustrates a perspective bottom view of a module, according to an embodiment of the present disclosure.

FIG. 2 illustrates a perspective bottom view of a module 106, according to an embodiment of the present disclosure. The module 106 includes a housing 130 that retains a plurality of UV light emitters 108 that are configured to emit UV light through the aperture 112. As shown, the module 106 includes a first plurality of UV light emitters 108a and a second plurality of UV light emitters 108b. The first plurality of UV light emitters 108a are contained within a first sub-housing 132, and the second plurality of UV light emitters 108b are contained within a second sub-housing 134 that is distinct from the first sub-housing 132. Each of the first sub-housing 132 and the second sub-housing 134 can contain more or less UV light emitters 108 than shown. Optionally, the module 106 can include a single sub-housing that retains all of the UV light emitters 108 shown in FIG. 2. In at least one embodiment, the module 106 can include a single UV light emitter 108, instead a plurality of UV light emitters 108.

Figure 3:
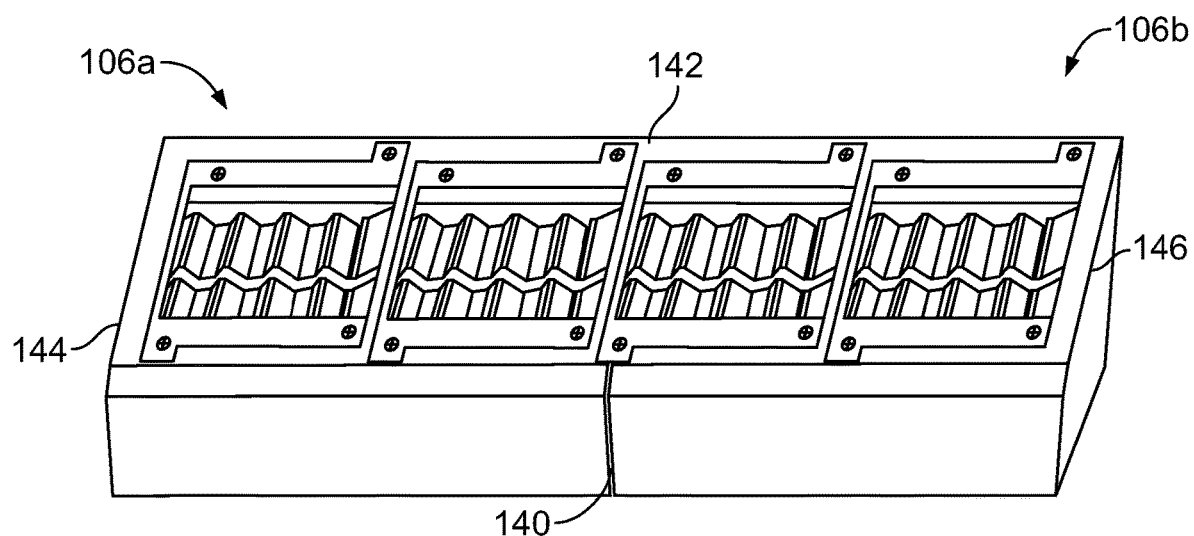
FIG. 3 illustrates a perspective bottom view of a first module coupled to a second module, according to an embodiment of the present disclosure.

FIG. 3 illustrates a perspective bottom view of a first module 106a coupled to a second module 106b, according to an embodiment of the present disclosure. A first end 140 of the first module 106a is coupled to an opposite second end 142 of the second module 106b. Optionally, the first module 106a and the second module 106b can be coupled together in a side-to-side fashion. Another module (not shown in FIG. 3) can be coupled to a second end 144 of the first module 106a. Further, another module (not shown in FIG. 3) can be coupled to a first end 146 of the second module 106b.

The modules 106a and 106b, as well as additional modules, can be stacked end-to-end, and/or side-to-side, as desired, to provide various illumination patterns. The first module 106a and the second module 106b can be removably coupled together, such as through one or more fasteners, bonding, a dove tail joint, a lap joint, a plug and socket connection, and/or the like. As such, the first module 106a and the second module 106b can be efficiently coupled together. Further, the first module 106a and the second module 106b can be disconnected, such as if one of the first module 106 or the second module 106b is in need of repair or is to be replaced.

Figure 4:
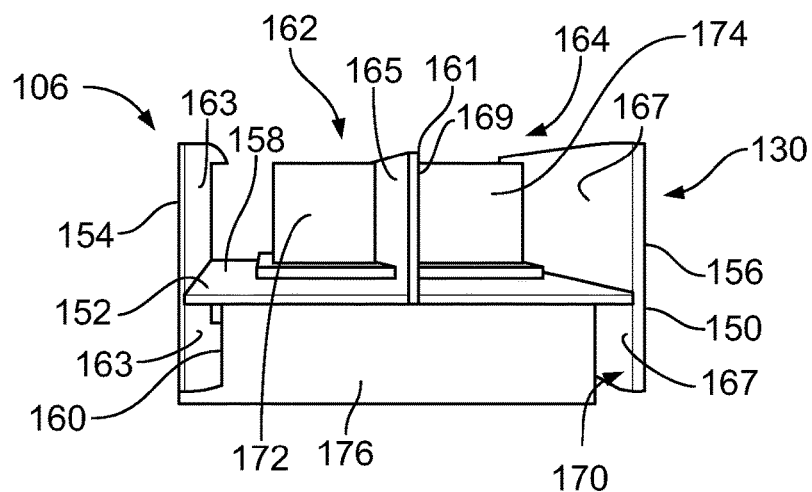
FIG. 4 illustrates a perspective end view of a module, according to embodiment of the present disclosure.
Figure 5:
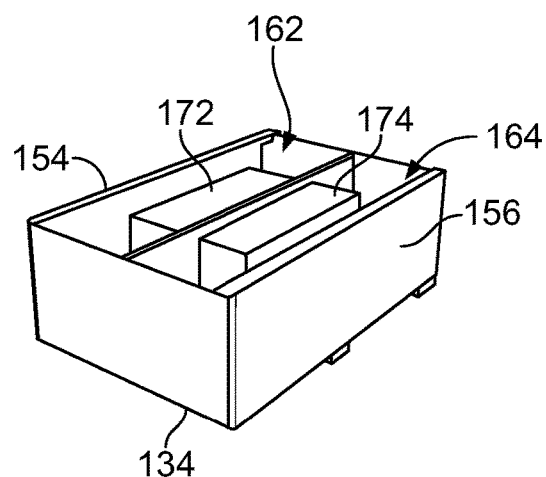
FIG. 5 illustrates a perspective top view of the module of FIG. 4.
Figure 6:
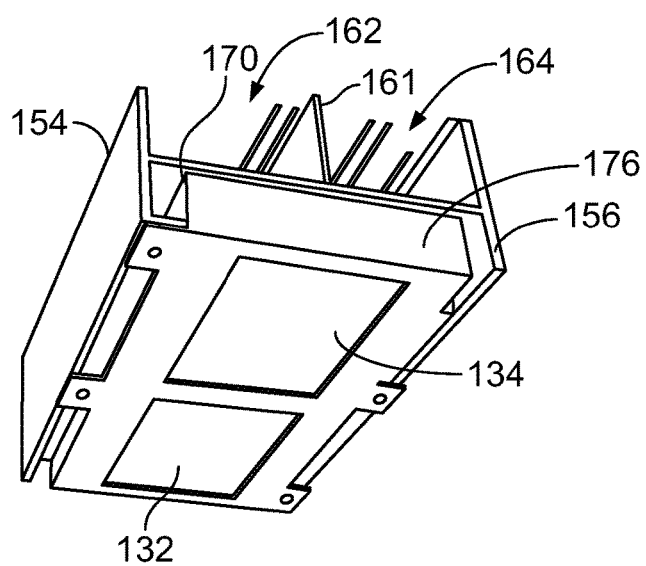
FIG. 6 illustrates a perspective bottom view of the module of FIG. 4.

FIG. 4 illustrates a perspective end view of a module 106, according to embodiment of the present disclosure. FIG. 5 illustrates a perspective top view of the module 106 of FIG. 4. FIG. 6 illustrates a perspective bottom view of the module 106 of FIG. 4. Referring to FIGS. 4-6, for the sake of clarity, certain outer wall portions of the module 106 are not shown in order show internal components.

In at least one embodiment, the housing 130 includes a bracket 150 having a platform 152 extending between opposite side walls 154 and 156. The platform 152 includes an upper surface 158 opposite from a lower surface 160. A dividing wall 161 upwardly extends from the upper surface 156. A first power chamber 162 is defined between the upper surface 158, an interior surface 163 of the side wall 154, and a first side surface 165 of the dividing wall 161. A second power chamber 164 is defined between the upper surface 158, an interior surface 167 of the side wall 156, and a second side surface 169 (opposite from the first side surface 165) of the dividing wall 161. An emitter chamber 170 is defined between the lower surface 158, the interior surface 163 of the side wall 154, and the interior surface 167 of the side wall 156.

A first power supply 172 is secured within the first power chamber 162. A second power supply 174 is secured within the second power chamber 164. Referring to FIGS. 1-6, the first power supply 172 and the second power supply 174 may be batteries and/or electrical power interfaces, connections, and/or the like that are configured to provide power to the UV light emitters 108.

In at least one embodiment, a frame 176 is secured within the emitter chamber 170, such as via one or more fasteners, bonding, and/or the like. The frame 176 retains the first sub-housing 132 and the second sub-housing 134. The UV light emitters 108 of the first sub-housing 132 and the second sub-housing 134 are electrically coupled to the first power supply 172 and the second power supply 174, respectively, such as through wires that pass through slots, channels, or other such openings formed in the platform 152.

The platform 152 separates and isolates the frame 176 (including the UV light emitters 108) from the first power supply 172 and the second power supply 174. Further, the dividing wall 161 separates and isolates first power supply 172 from the second power supply 174. In at least one embodiment, the first power supply 172 and the second power supply 174 can be high voltage power supplies (such as 2 kV), and therefore the separation and isolation therebetween and in relation to the frame 176 ensures reliable and efficient operation.

As shown, the first power supply 172 and the second power supply 174 are stacked above the frame 176, which retains the first sub-housing 132 and the second sub-housing 134. Optionally, a single power supply can be used to provide power to the UV light emitters 108 of the first sub-housing 132 and the second sub-housing 134. In at least one embodiment, the bracket 150 may not include the dividing wall 161. In at least one other embodiment, the power suppl(ies) can be remote from the module 106.

Figure 7:
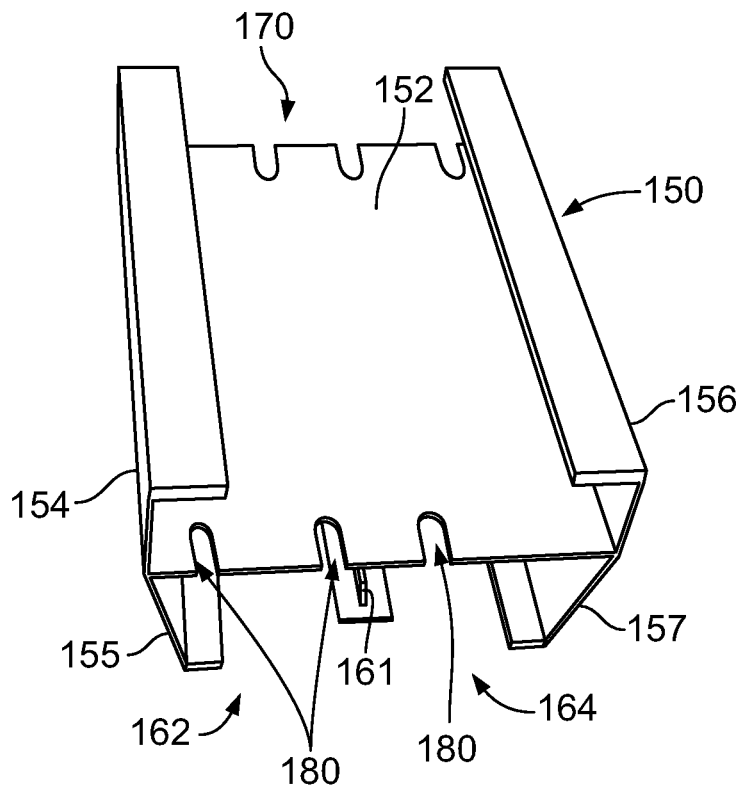
FIG. 7 illustrates a perspective bottom view of a bracket, according to an embodiment of the present disclosure.
Figure 8:
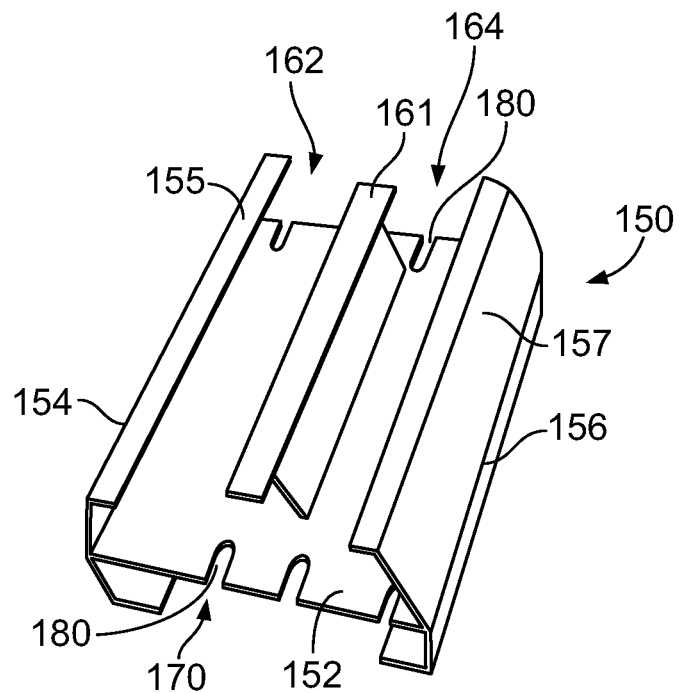
FIG. 8 illustrates a perspective top view of the bracket of FIG. 7.

FIG. 7 illustrates a perspective bottom view of the bracket 150, according to an embodiment of the present disclosure. FIG. 8 illustrates a perspective top view of the bracket 150 of FIG. 7. Referring to FIGS. 7 and 8, the bracket 150 can include one or more passages 180 (such as slots) formed through the platform 152. Referring to FIGS. 1-8, the passages 180 allow for wiring to be routed between the UV light emitters 108 and the power supplies 172 and/or 174, for example. Optionally, the bracket 150 may not include the passages 180. Instead, wiring can be routed around end edges of the platform 152, for example.

As shown, the side walls 154 and 156 can includes inwardly-canted segments 155 and 157, respectively, bounding the first power chamber 162 and the second power chamber 164, respectively. Free ends of the inwardly-canted segments angle toward the dividing wall 161. The inwardly-canted segments 155 and 157 provide a more compact bracket 150, which takes up less space. Optionally, the side walls 154 and 156 can also, or alternatively, include inwardly-canted segments. Alternatively, the bracket 150 may not include inwardly-canted segments.

Figure 9:
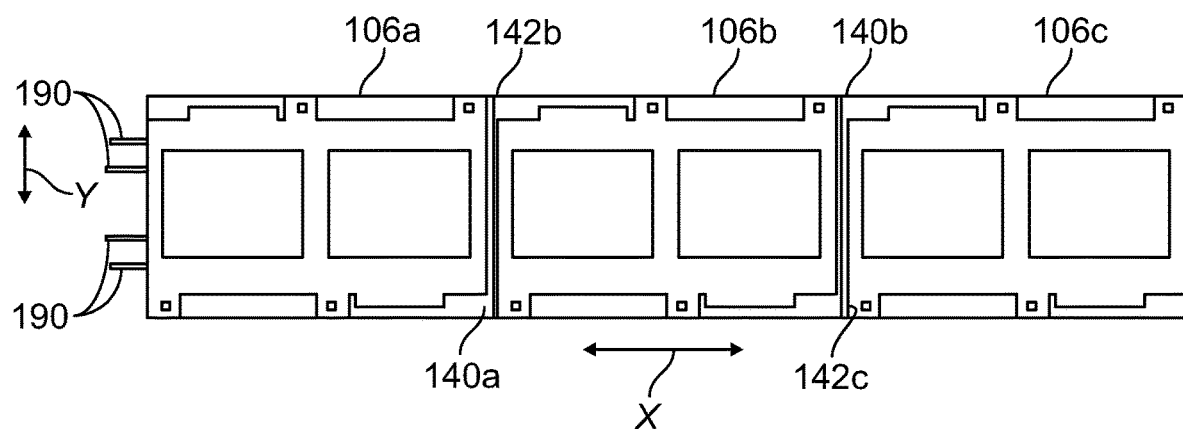
FIG. 9 illustrates a bottom view of a plurality of modules coupled together, according to an embodiment of the present disclosure.

FIG. 9 illustrates a bottom view of a plurality of modules 106a, 106b, and 106c coupled together, according to an embodiment of the present disclosure. A first end 140a of the module 106a is secured to a second end 142b of the module 106b. A first end 140b of the module 106b is secured to a second end 142c of the module 106c. As shown, the modules 106a, 106b, and 106c are linearly aligned in the X direction in an end-to-end configuration. Optionally, one or more of the modules 106a, 106b, and 106c can be aligned in the Y direction a side-to-side configuration. Wiring 190 is routed to each of the modules 106a, 106b, and 106c.

Figure 10:
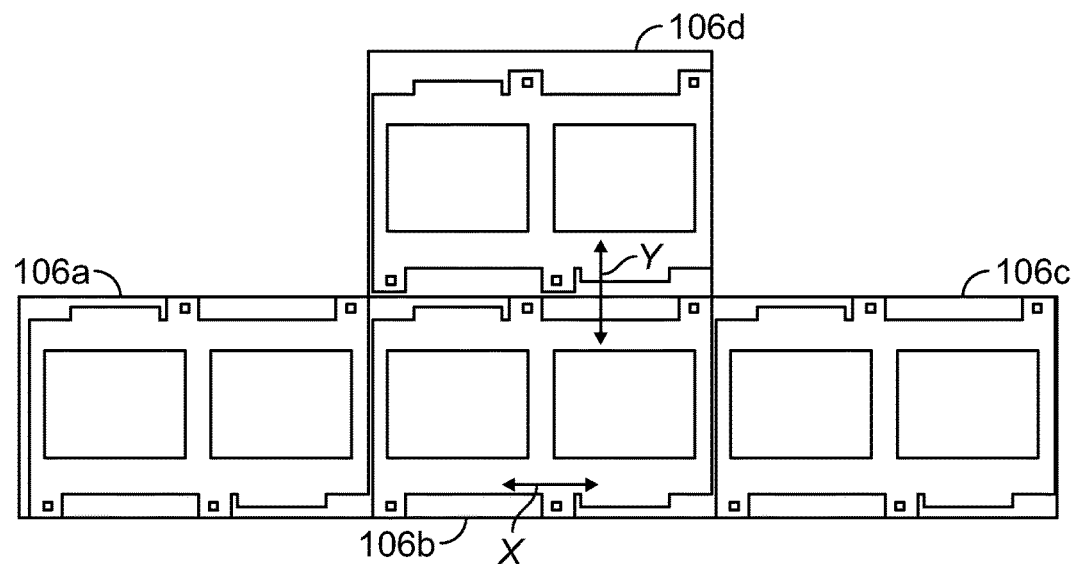
FIG. 10 illustrates a bottom view of a plurality of modules coupled together, according to an embodiment of the present disclosure.

FIG. 10 illustrates a bottom view of a plurality of modules 106a, 106b, 106c, and 106d coupled together, according to an embodiment of the present disclosure. As shown, the module 106d can be secured to the module 106b in a side-to-side fashion. Optionally, the module 106d can be coupled to the module 106a or 106c. In at least one other embodiment, additional modules (not shown) can be coupled to each of the modules 106a, 106b, or 106c in a side-to-side configuration.

Figure 11:
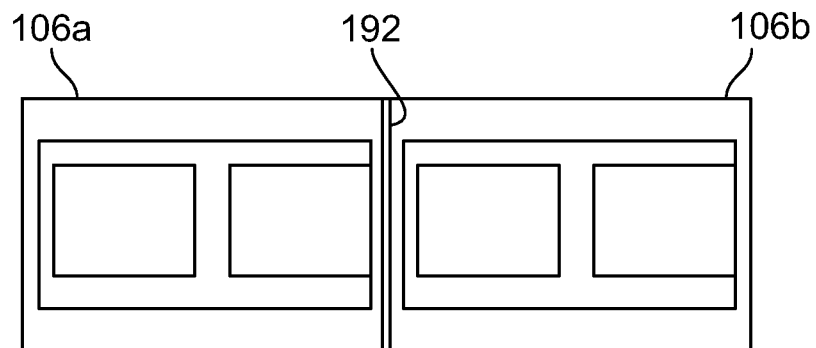
FIG. 11 illustrates a bottom view of a first module coupled to a second module, according to an embodiment of the present disclosure.

FIG. 11 illustrates a bottom view of a first module 106a coupled to a second module 106b, according to an embodiment of the present disclosure. The first module 106a couples to the second module 106b via bonding at a bond interface 192 therebetween.

Figure 12:
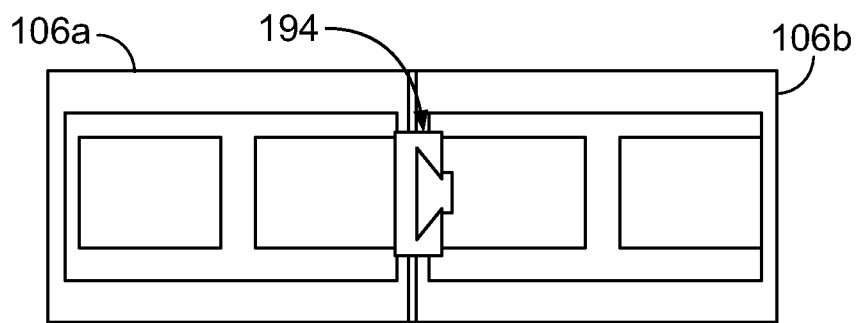
FIG. 12 illustrates a bottom view of a first module coupled to a second module, according to an embodiment of the present disclosure.

FIG. 12 illustrates a bottom view of a first module 106a coupled to a second module 106b, according to an embodiment of the present disclosure. The first module 106a couples to the second module 106b via a connecting joint 194, such as a dove tail joint.

Figure 13:
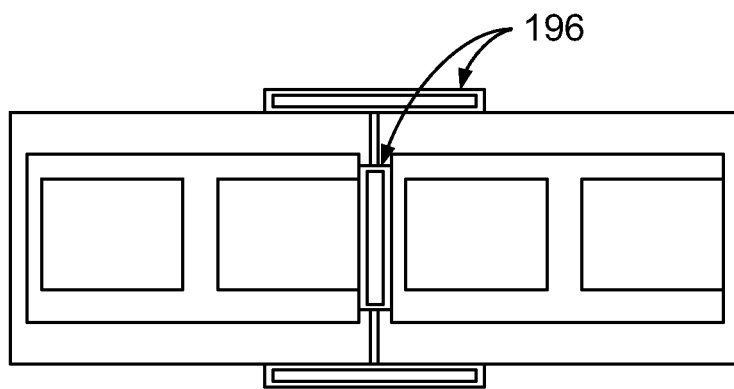
FIG. 13 illustrates a bottom view of a first module coupled to a second module, according to an embodiment of the present disclosure.

FIG. 13 illustrates a bottom view of a first module 106a coupled to a second module 106b, according to an embodiment of the present disclosure. The first module 106a couples to the second module 106b via one or more connecting joints 196, such as lap toil joints at connected ends and/or sides. Fasteners, such as screws or bolts, and/or bonding can be used to secure the connecting joints 196 to the first module 106a and the second module 106b.

Figure 14:
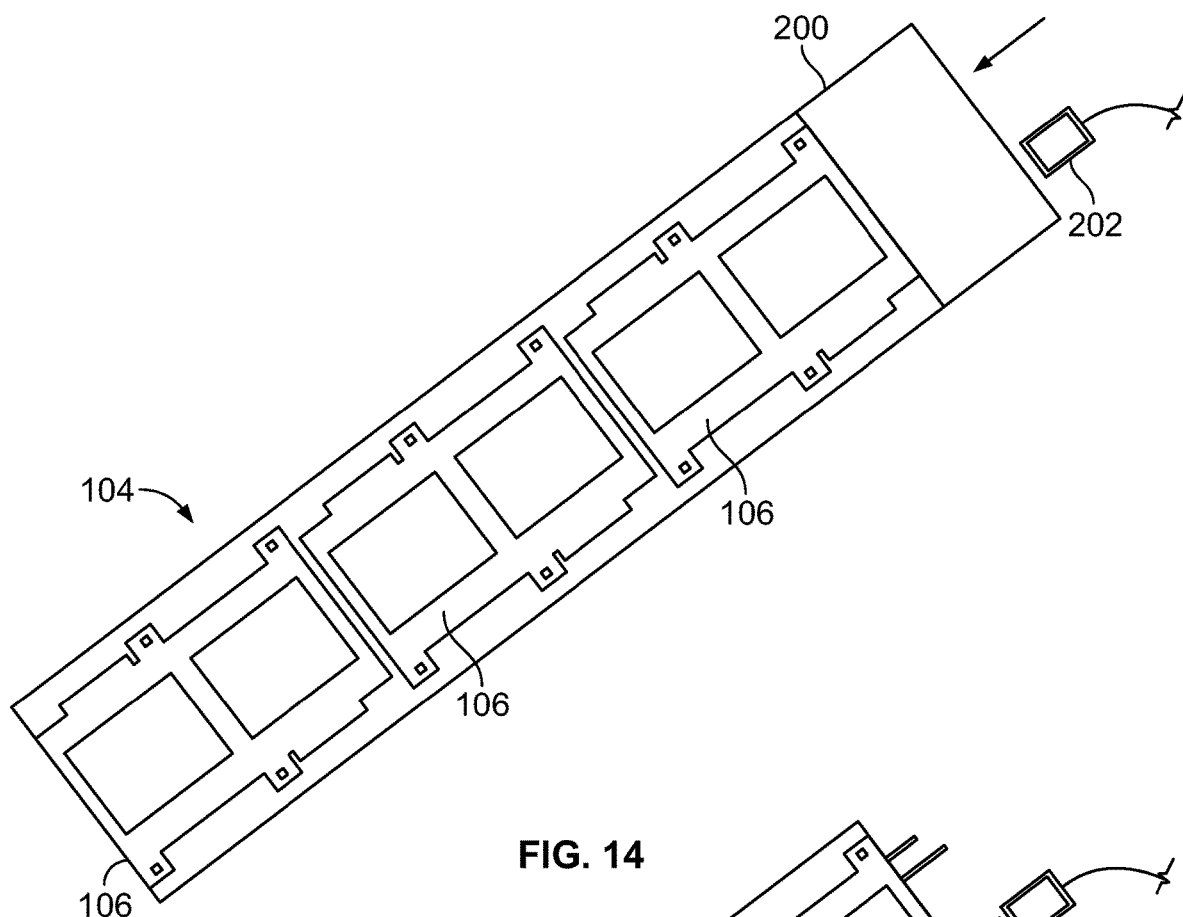
FIG. 14 illustrates a bottom view of a UV lamp having a plurality of modules, according to an embodiment of the present disclosure.

FIG. 14 illustrates a bottom view of the UV lamp 104 having a plurality of modules 106, according to an embodiment of the present disclosure. The UV lamp 104 can include a battery 200, such as 24 V battery, that provides power to the power supplies of the modules 106. In at least one embodiment, the battery 200 is configured to mate with a power cord 202 to be recharged.

Figure 15:
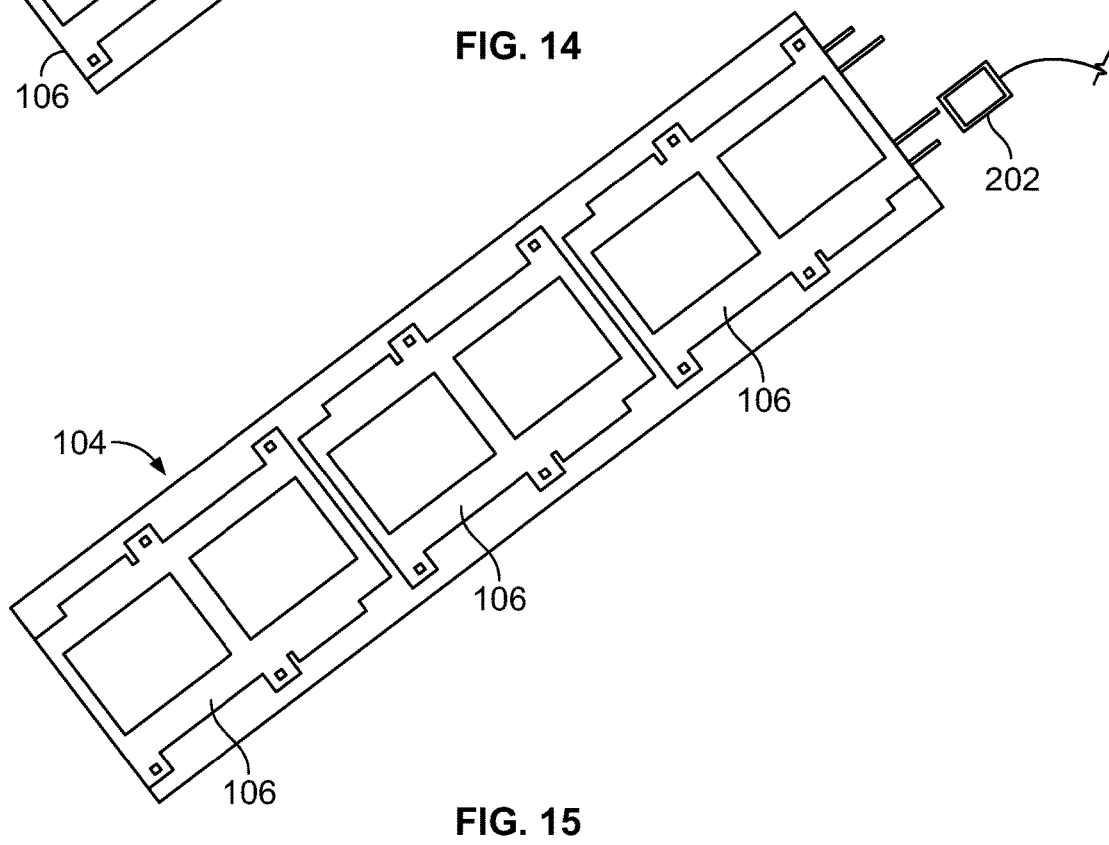
FIG. 15 illustrates a bottom view of a UV lamp having a plurality of modules, according to an embodiment of the present disclosure.

FIG. 15 illustrates a bottom view of the UV lamp 104 having a plurality of modules 106, according to an embodiment of the present disclosure. In this embodiment, the UV lamp 104 may not include a battery. Instead, the UV lamp receives power from the power cord 202.

Figure 16:
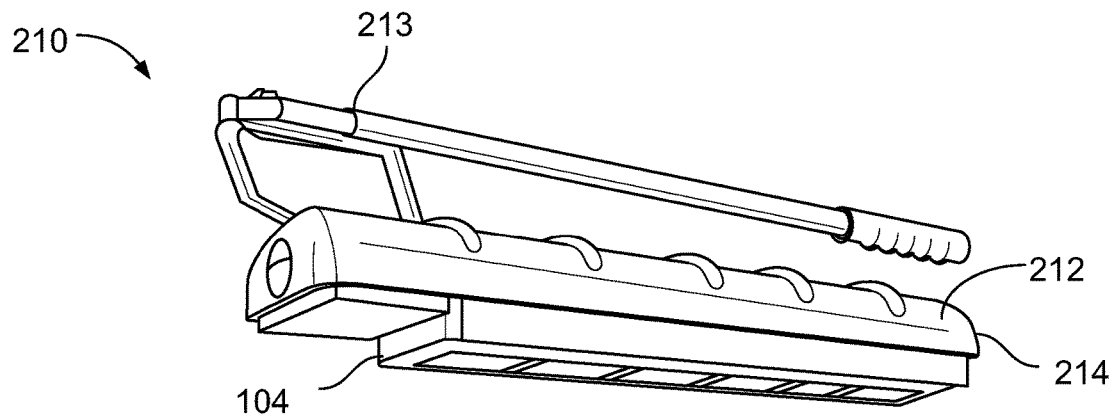
FIG. 16 illustrates a perspective lateral view of a wand assembly including a UV lamp, according to an embodiment of the present disclosure.
Figure 17:
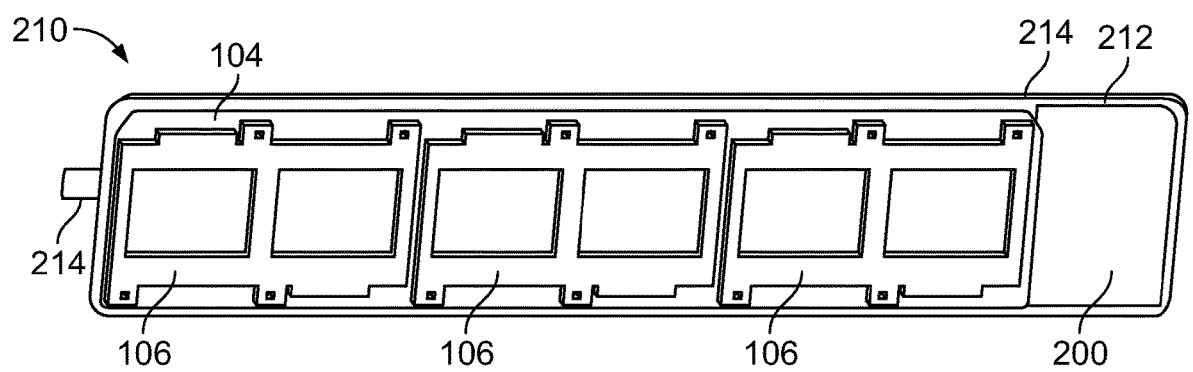
FIG. 17 illustrates a bottom view of the wand assembly of FIG. 16.

FIG. 16 illustrates a perspective lateral view of a wand assembly 210 including the UV lamp 104, according to an embodiment of the present disclosure. FIG. 17 illustrates a bottom view of the wand assembly of FIG. 16. Referring to FIGS. 16 and 17, the wand assembly 210 includes a sanitizing head 212 coupled to a handle 213. The sanitizing head 212 includes a shroud 214 that retains the UV lamp 104. The battery 200 can be retained within the shroud 214.

In at least one embodiment, the sanitizing head 212 is configured to move relative to the handle 213. For example, the sanitizing head 212 can be extended and/or rotated relative to the handle 213. In at least one other embodiment, the sanitizing head 212 is fixed in relation to the handle 213. The wand assembly 210 can include the UV lamp 104 having a plurality of modules 106, as described with respect to any of FIGS. 1-15.

Figure 18:
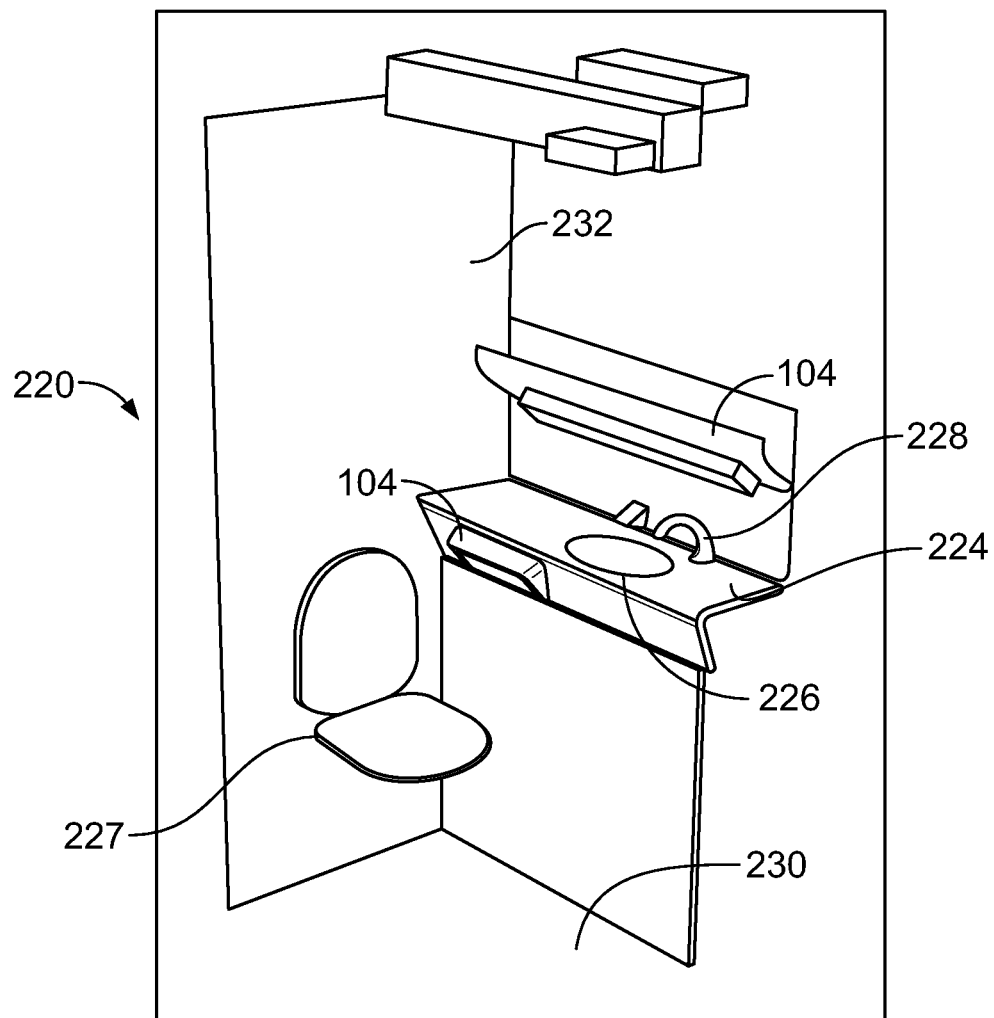
FIG. 18 illustrates a perspective internal view of a lavatory, according to an embodiment of the present disclosure.

FIG. 18 illustrates a perspective internal view of a lavatory 220, according to an embodiment of the present disclosure. The lavatory 220 may be within an internal cabin of a vehicle, such as a commercial aircraft. The lavatory 220 includes a toilet 222 and a counter 224 having a sink 226 and faucet 228. One or more UV lamps 104 are disposed within the lavatory 220. The UV lamps 104 are configured as described with respect to any of FIGS. 1-15.

The UV lamps 104 are configured to emit UV light to disinfect one or more components within the lavatory 220, such as the toilet 222, the counter 224, the sink 226, the faucet 228, the floor 230, one or more walls 232, and/or the like. In at least one embodiment, the UV lamps 104 can be fixed in position. In at least one other embodiment, the UV lamps 104 can be configured to move. For example, the UV lamps 104 can be moved between stowed positions and deployed positions.

Figure 19:
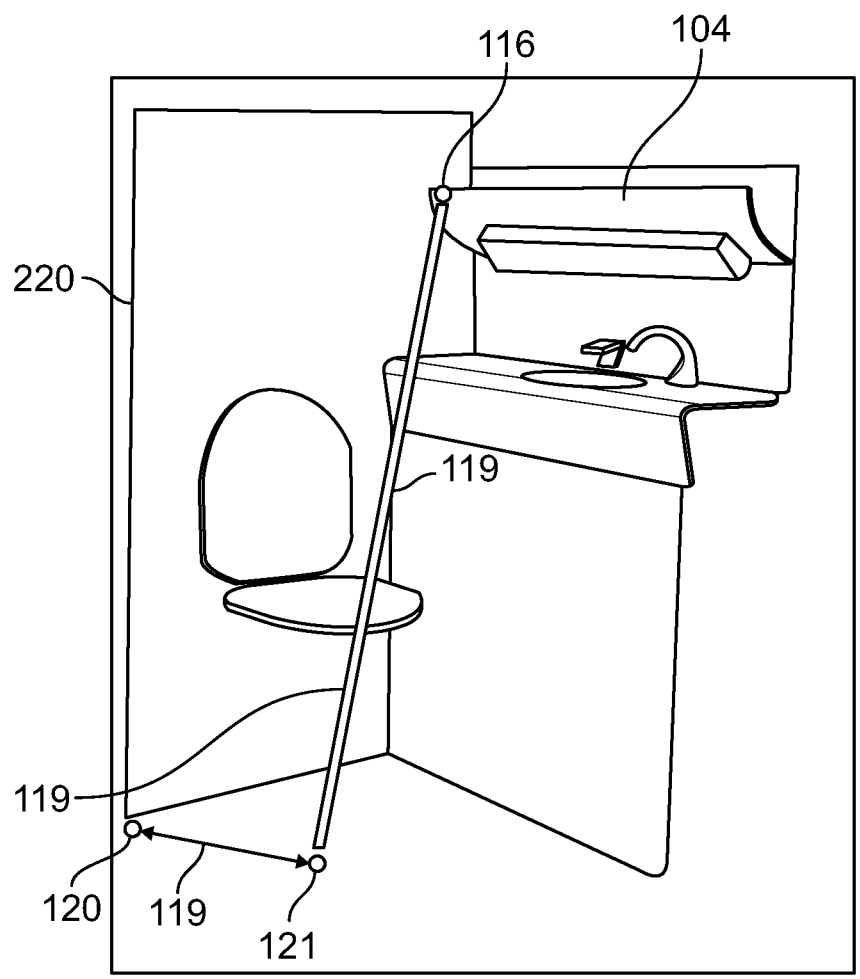
FIG. 19 illustrates a perspective internal view of the lavatory, according to an embodiment of the present disclosure.

FIG. 19 illustrates a perspective internal view of the lavatory 220, according to an embodiment of the present disclosure. Referring to FIGS. 1 and 19, in this embodiment, the UV lamp 104 includes the IR sensor 116 that receives the IR light signal 119 from the IR source 120. The IR source 120 is configured to emit the IR light signal 119 through an area in which an individual would be if occupying the lavatory 220.

The IR sensor 116 may be aligned with the IR source 120 to directly receive the IR light signal 119 from the IR source 120. Optionally, the IR source 120 may be configured to emit the IR light signal 119 at a reflector, such as a mirror, that reflect the IR light signal 119 to the IR source 120.

The IR sensor 116 can be mounted directly to the UV lamp 104, such as on a housing. In at least one embodiment, the IR sensor 116 can be secured to a module 106. In at least one embodiment, multiple modules 106 include an IR sensor 116. In at least one other embodiment, the IR sensor 116 is remote (e.g., separate and spaced apart) from the UV lamp 104.

As shown, the IR sensor 116 can be secured to an end or corner of the UV lamp 104. The IR sensor 116 is configured to receive the IR light signal 119 either directly from the IR source 120 or indirectly from the IR source 120 as reflected from one or more reflectors 121. The IR light signal 119 can be a laser or narrow non-laser optical signal, for example.

As shown, the IR light signal 119 is configured to extend through a portion of the lavatory 220 such that a person entering or exiting the room crosses the path of and interrupts the IR light signal 119. As the path between the IR source 120 and the IR sensor 116 is interrupted, the IR sensor 116 does not receive the IR light signal 119. When the IR sensor 116 does not receive the IR light signal 119, the control unit 118 does not receive the sensed IR signal 122 from the IR sensor 116. Further, the IR light signal 119 is directed such that an individual within the lavatory 220 would interrupt the IR light signal 119.

Figure 23:
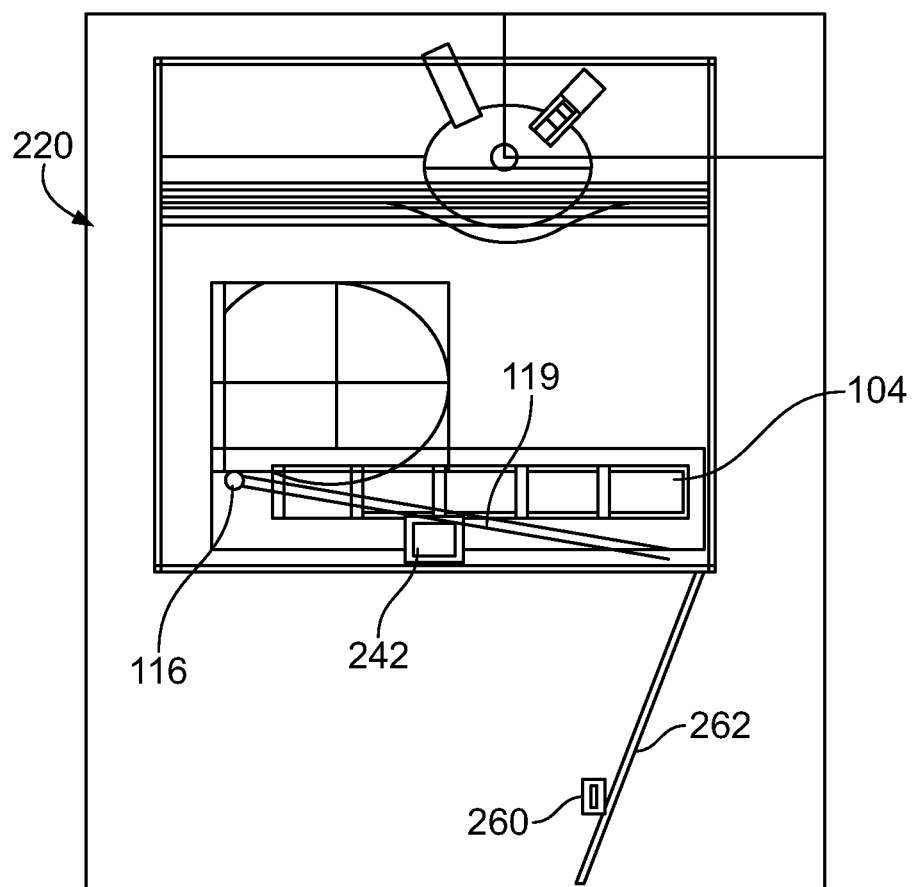
FIG. 23 illustrates a top plan view of a lavatory, according to an embodiment of the present disclosure.
Figure 24:
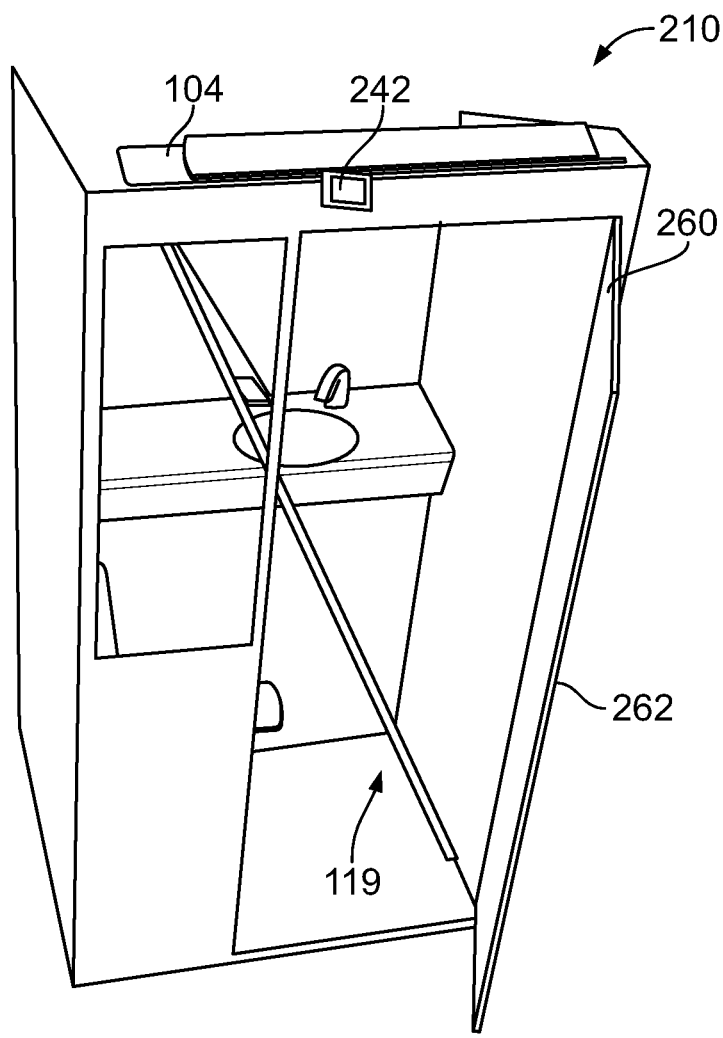
FIG. 24 illustrates a perspective internal view of the lavatory of FIG. 23.

The control unit 118 operates to ensure that the UV light emitters 108 are deactivated when an individual is within the lavatory 220 (or other such room in which the UV lamp 104 is used). By communicating with the IR sensor 116 (and optionally, the door sensor 242 as shown in FIGS. 23 and 24), the control unit 118 determines whether the room is occupied or unoccupied. If occupied, the control unit 118 deactivates the UV light emitters 108. If unoccupied, the control unit 118 can activate the UV light emitters 108 to disinfect one or more components within the room.

Figure 20:
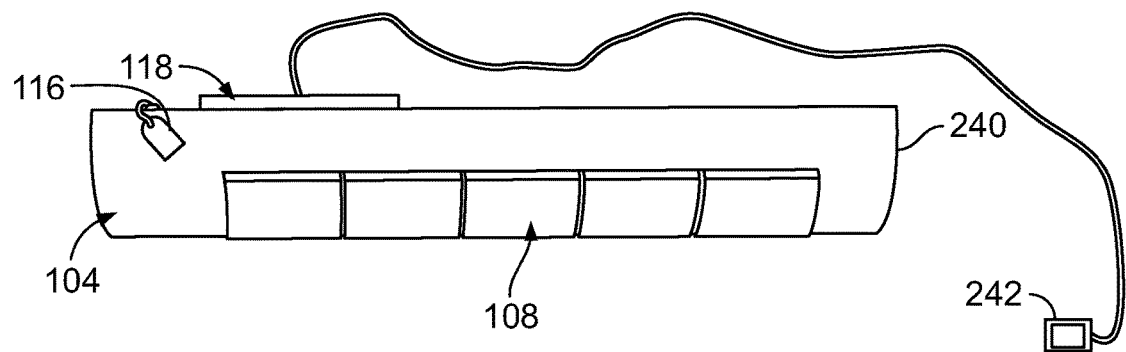
FIG. 20 illustrates a perspective bottom view of a UV lamp, according to an embodiment of the present disclosure.

FIG. 20 illustrates a perspective bottom view of the UV lamp 104, according to an embodiment of the present disclosure. Referring to FIGS. 1 and 2, the UV lamp 104 104 includes a housing 240 having a plurality of UV light emitters 108, whether within modules 106 or not. The IR sensor 116 is secured to the housing 240 and is oriented in a direction to receive the IR light signal 119.

The control unit 118 is in communication with the IR sensor 116 and the UV light emitters 108. In at least one embodiment, a door sensor 242 is also in communication with the control unit 118, such as through one or more wired or wireless connections. For example, the door sensor 242 is a Hall-effect sensor. The door sensor 242 is configured to detect opening and closing of a door of a room, such as the lavatory 220 shown in FIGS. 18 and 19. The control unit 118 selectively activates and deactivates the UV light emitters 108 based on IR signals (for example reception of such IR signal(s) and lack of reception of such IR signal(s) received from the IR sensor 116 and door signals (for example, signals indicating that the door is open or closed) received from the door sensor 242. Optionally, the control unit 118 is not in communication with a door sensor.

Figure 21:
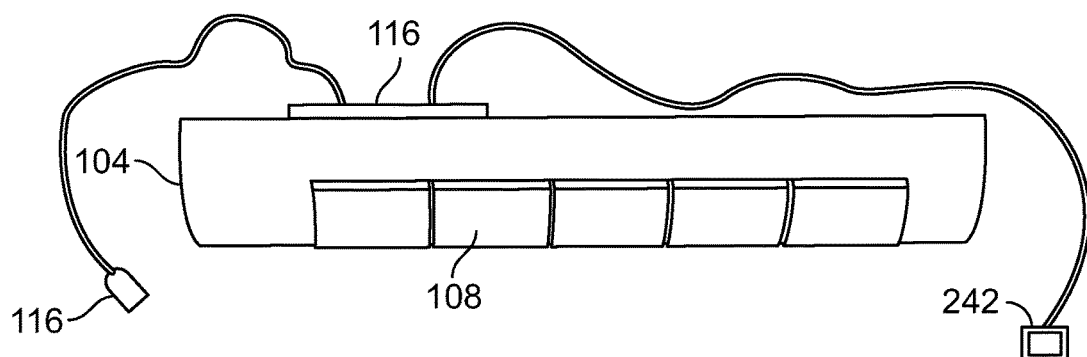
FIG. 21 illustrates a perspective bottom view of a UV lamp, according to an embodiment of the present disclosure.

FIG. 21 illustrates a perspective bottom view of the UV lamp 104, according to an embodiment of the present disclosure. In this embodiment, the IR sensor 116 is remotely located from the UV lamp 104, and is in communication with the control unit 118 through one or more wired or wireless connections.

Figure 22:
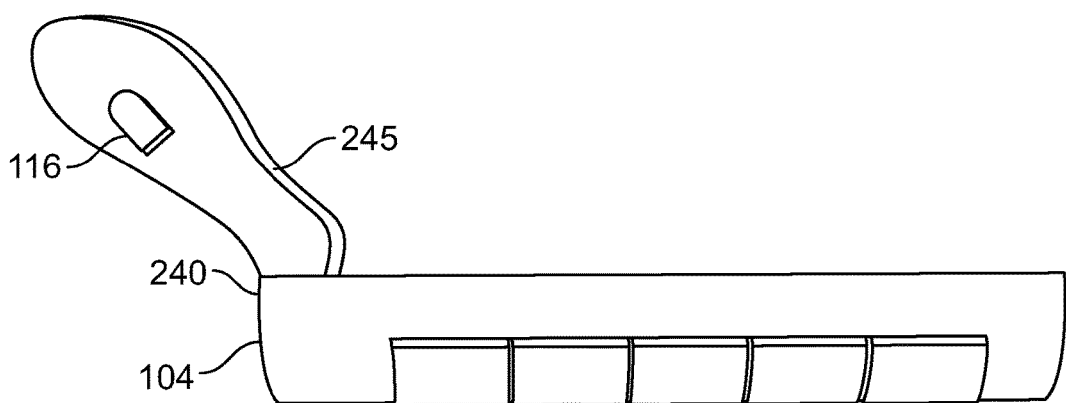
FIG. 22 illustrates a perspective bottom view of a UV lamp, according to an embodiment of the present disclosure.

FIG. 22 illustrates a perspective bottom view of the UV lamp 104, according to an embodiment of the present disclosure. As shown, the housing 240 can include an extension 245. The IR sensor 116 can be mounted on the extension 245.

FIG. 23 illustrates a top plan view of the lavatory 220, according to an embodiment of the present disclosure. FIG. 24 illustrates a perspective internal view of the lavatory 220 of FIG. 23. Referring to FIGS. 1 and 19-24, the door sensor 242, such as a Hall effect sensor, is configured to cooperate with a magnet 260 positioned on the door 262 of the lavatory 220 to determine when the door 262 is opened or closed. For example, when the magnet 260 touches or is in close proximity (such as within 6 inches or less) of the door sensor 242, the door sensor 242 outputs a signal to the control unit 118 that the door 262 is closed. In at least one embodiment, the door sensor 242 can be secured to the housing 240 of the UV lamp 104.

In at least one embodiment, the control unit 118 deactivates the UV light emitters 108 of the UV lamp 104 in response to the IR sensor 116 not receiving the sensed IR signal 122 from the IR sensor 116. Conversely, the control unit 118 activates the UV light emitters 108 to disinfect one or more components within the lavatory 220 in response to receiving the sensed IR signal 122 from the IR sensor 116 and receiving a signal from the door sensor 242 indicating that the door 262 is closed. In at least one embodiment, in response to receiving a signal from the door sensor 242 indicating that the door 262 is opened, the control unit 118 deactivates the UV light emitters 108, even if the control unit 118 receives the sensed IR signal 122 from the IR sensor 116.

Figure 25:
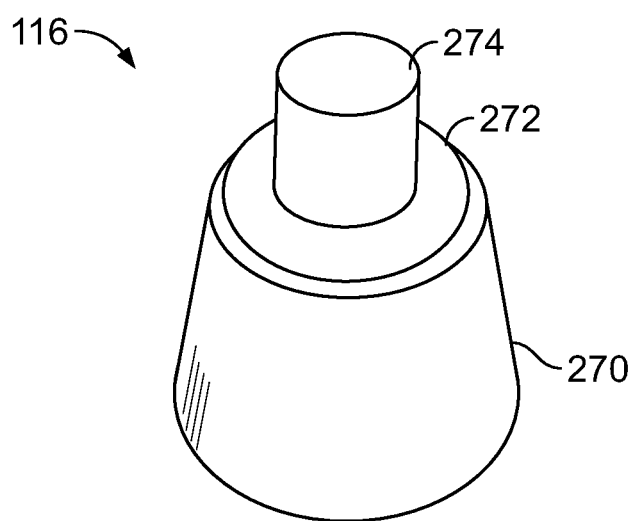
FIG. 25 illustrates a perspective view of an infrared sensor, according to an embodiment of the present disclosure.

FIG. 25 illustrates a perspective view of the IR sensor 116, according to an embodiment of the present disclosure. In at least one embodiment, the IR sensor 116 includes a socket 270 that moveably retains a ball 272. The ball 272 retains a sensing element 274 that is configured to receive and detect an IR light signal. The ball and socket configuration shown in FIG. 25 allows the sensing element 274 to be moved to a desired orientation and alignment so as to receive the IR light signal. Optionally, the IR sensor 116 may not include a movable element, such as the ball 272 moveably retained within the socket 270.

Referring to FIGS. 1 and 19-25, in at least one embodiment, the control unit 118 activates the UV light emitters 108 in response to determining that the lavatory 220 (or other such room) is vacated and unoccupied. For example, in response to reception of a signal from the door sensor 242 that the door 262 is opened and the sensed IR light signal 122 for at least one second, followed by reception of a signal from the door sensor 242 that the door 262 is closed and the sensed IR light signal 122 for at least one additional second, the control unit 118 activates the UV light emitters 108 for a predetermined sanitizing period (such as 5 seconds). If the control unit 118 detects that the door 262 is opened during the sanitizing period, the control unit 118 immediately deactivates the UV light emitters 108.

Further, if the control unit 118 detects that IR sensor 116 is not receiving the IR light signal 119 (such as by not receiving the sensed IR light signal 122 from the IR sensor), the control unit 118 deactivates the UV light emitters 108. Such an interruption of the IR light signal 119 triggers a reset event, in which the control unit 118 may then reactivate the UV light emitters 108 after determining that the door 262 has been opened, reception of the sensed IR light signal 122 from the IR sensor 116, the door 262 is subsequently closed, and further reception of the sensed IR light signal 122 from the IR sensor 116.

Figure 26:
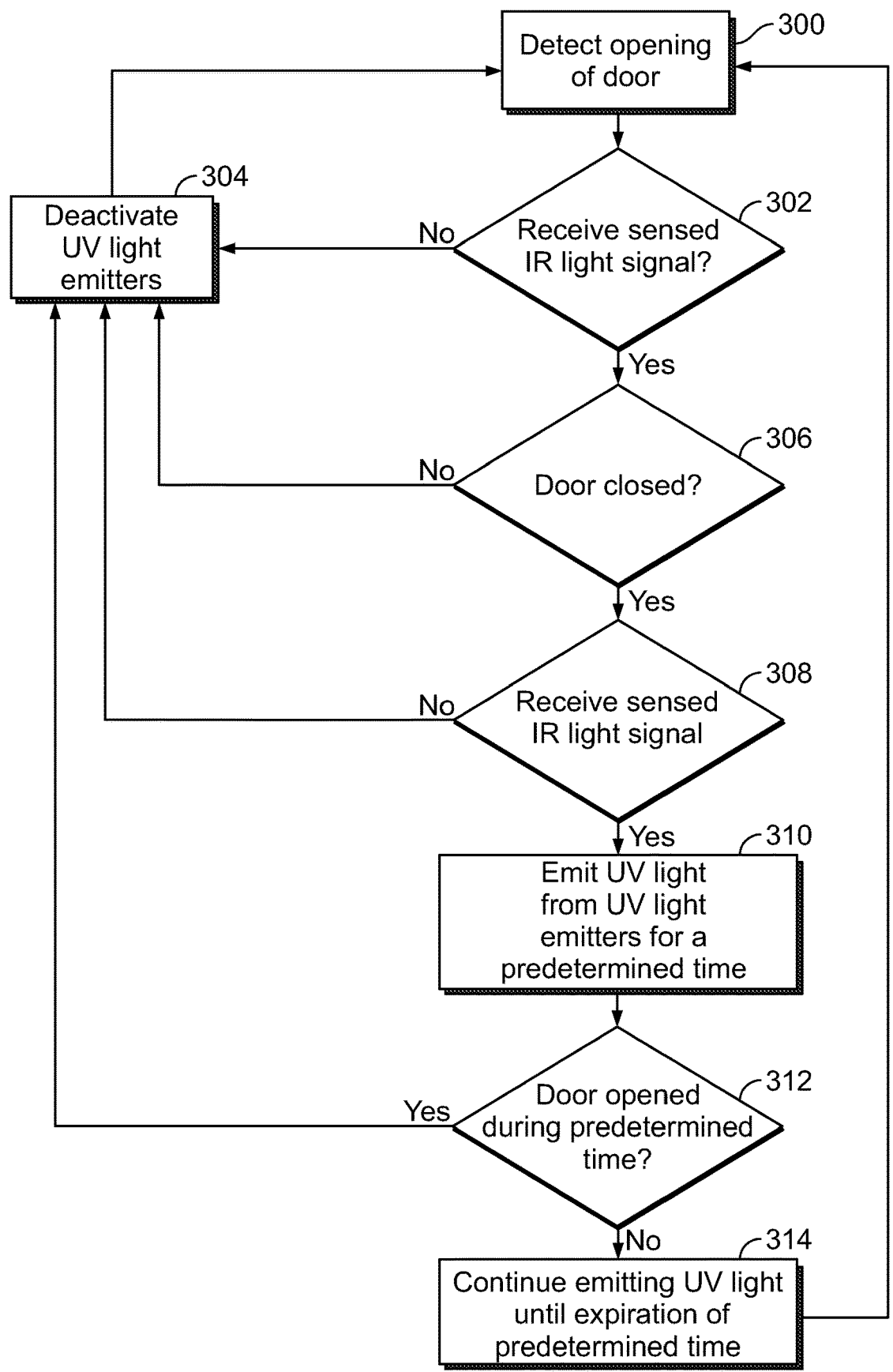
FIG. 26 illustrates a flow chart of a method of operating a UV lamp, according to an embodiment of the present disclosure.

FIG. 26 illustrates a flow chart of a method of operating a UV lamp, according to an embodiment of the present disclosure. Referring to FIGS. 1 and 19-26, at 300, the control unit 118 determines an opening of the door 262, such as via a signal received from the door sensor 242. At 302, the control unit 118 determines if the sensed IR light signal 122 is received from the IR sensor 116. If not, the method proceed to 304, at which the control unit 118 deactivates the UV light emitters 108, and the method then returns to 300.

If, however, the sensed IR light signal 122 is received from the IR sensor 116 at 302, the control unit 118 determines if the door 262 is closed, such as via a signal received from the door sensor 242. If the door is not closed, the method returns to 304.

If, however, the door 262 is closed, the control unit 118 determines if the sensed IR light signal 122 is received at 308. If not, the method returns to 304.

If, however, the control unit 118 determines that the sensed IR light signal 122 is received at 308, the control unit 118 operates the UV lamp 104 at 310 to emit the UV light from the UV light emitters 108 for a predetermined sanitizing time (such as 3-5 seconds). If, at 312, the control unit 118 determines that the door 262 is opened during the predetermined sanitizing time, the method returns to 304, at which the control unit 118 immediately deactivates the UV light emitters 304.

If, however, the door is not opened during the predetermined sanitizing time at 312, the method proceeds from 312 to 314, at which the control unit 118 operates the UV light emitters 108 to continue to emit the UV light until an expiration of the predetermined time, at which point the UV light emitters 108 are deactivated. The process then returns to 300.

Figure 27:
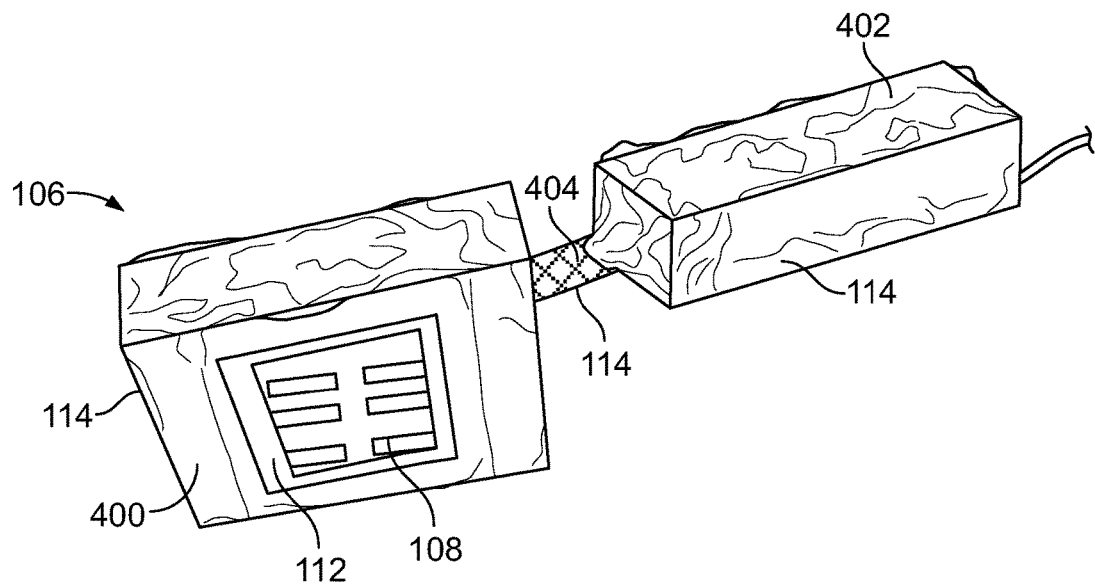
FIG. 27 illustrates a perspective view of a module, according to an embodiment of the present disclosure.

FIG. 27 illustrates a perspective view of a module 106, according to an embodiment of the present disclosure. The module 106 includes a sub-housing 400 retaining one or more UV light emitters 108. The sub-housing 400 is coupled to a power supply 402 through a cable 404. In contrast to the embodiments shown in FIGS. 4-6, the sub-housing 400 and the power supply 402 may not be secured within a common bracket. Optionally, the sub-housing 400 and the power supply 402 may be secured to a bracket, such as the bracket 150 shown and described with respect to FIGS. 4-6, for example.

An EMI shield 114 (for example, a first EMI shield) is disposed around portions of the sub-housing 400. In at least one embodiment, the EMI shield 114 is disposed around all portions of the sub-housing 400, except the aperture 112. As an example, the EMI shield 114 is a metal foil (for example, a stainless steel, aluminum, or the like foil) that extends around portions of the sub-housing 400. The EMI shield 114 blocks, attenuates, or otherwise hinders EMI that may be generated by operation of the UV light emitters 108 from passing therethrough (and/or blocks EMI from passing into the sub-housing 400).

The EMI shield 114 (for example, a second EMI shield) may also extend around portions of the power supply 402 and/or the cable 404. For example, the EMI shield 114 may wrap around all portions of the power supply 402 and/or the cable 404. In at least one embodiment, the EMI shield 114 covers an entirety of the module 106 including the sub-housing 400, the power supply 402, and the cable 404, except for the aperture 112. The EMI shield 114 blocks, attenuates, or otherwise hinders EMI from passing between the sub-housing 400 and the power supply 402.

Further, by separating the sub-housing 400 from the power supply 402 (and connecting via the cable 404), the module 106 may be more readily integrated and used in certain confined areas in which a common housing retaining both may be too large. The sub-housing 400 as shown in FIG. 27 has a low profile and may fit into smaller spaces.

The EMI shield 114 may be used with any of the embodiments described herein. Further, a module including the sub-housing 400 separated from the power supply 402 (as shown in FIG. 27) may be used with any of the embodiments described herein, whether with the EMI shield 114 or without the EMI shield 114.

Figure 28:
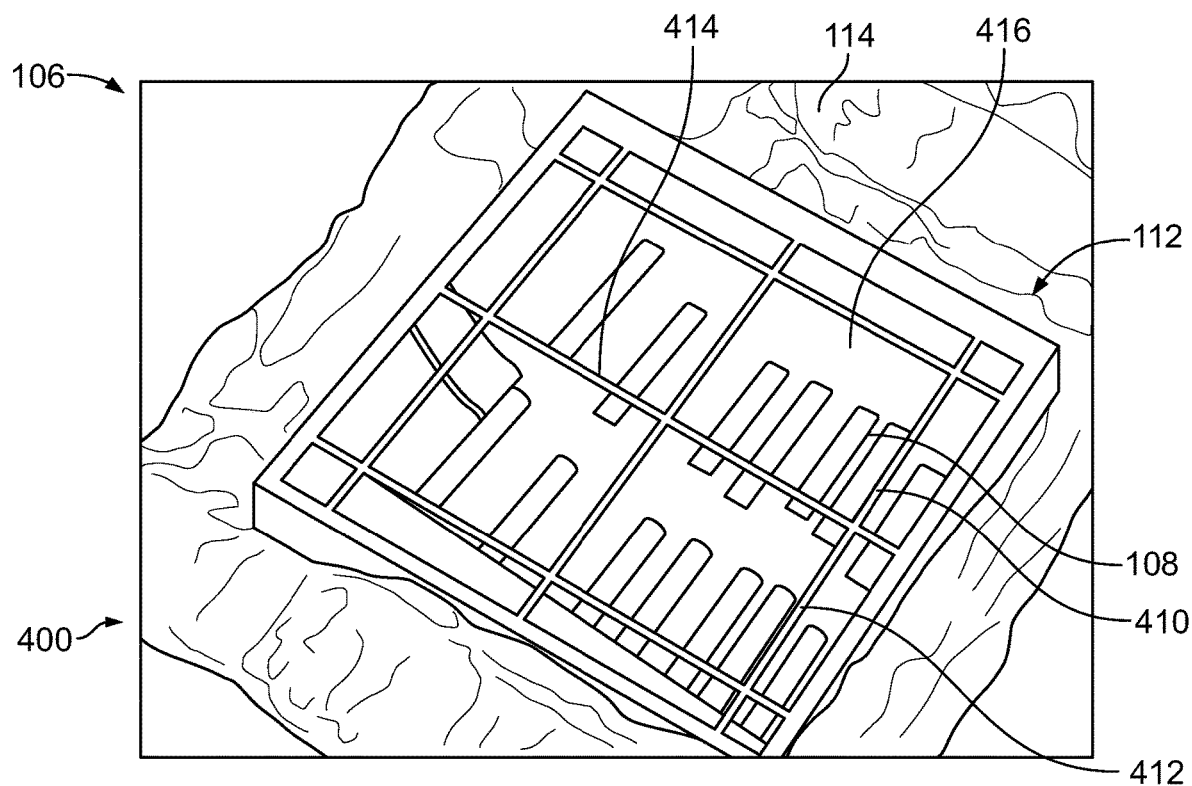
FIG. 28 illustrates a perspective bottom view of a sub-housing of the module of FIG. 27.

FIG. 28 illustrates a perspective bottom view of the sub-housing 400 of the module 106 of FIG. 27. In at least one embodiment, an EMI grid 410 is disposed within the aperture 112. The EMI grid 410 includes a plurality of longitudinal beams 412 that intersect a plurality of lateral beams 414, defining passages 416 therebetween. The beams 412 and 414 may have a thickness between 0.001"-0.010", for example. In this manner, the EMI grid 410 can be a mesh screen or cage, for example. The EMI grid 410 also hinders passage of EMI into or out of the module 106. In at least one embodiment, the EMI grid 410 can be formed of stainless steel. Alternatively, the module 106 does not include the EMI grid 410.

Figure 29:
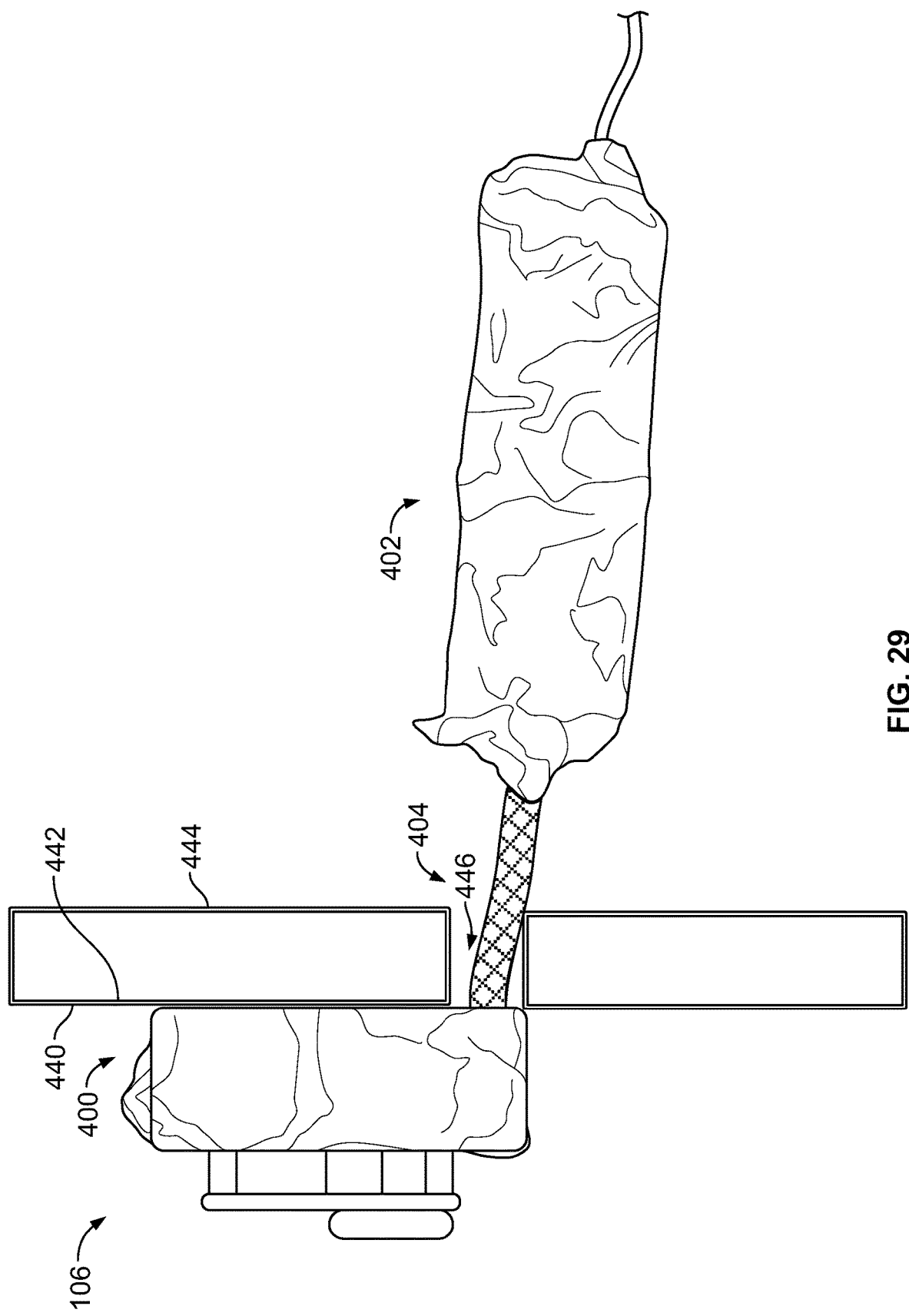
FIG. 29 illustrates a lateral view of the module of FIG. 27 secured to a wall, according to an embodiment of the present disclosure.

FIG. 29 illustrates a lateral view of the module 106 of FIG. 27 secured to a wall 440, according to an embodiment of the present disclosure. The sub-housing 400 can be mounted on a first surface 442 (such as an outer or inner surface) of the wall 440, and the power supply 402 can be disposed behind the wall 440. For example, the power supply 402 can be secured behind a second surface 444 (opposite from the first surface) of the wall 440. An opening 446 formed through the wall 440 is configured to allow the cable 404 to pass therethrough. In this manner, the wall 440 also isolates the sub-housing 400 from the power supply 402.

The wall 440 may be a portion of a room. For example, the wall 440 may be a wall of a lavatory, such as the lavatory 220 shown in FIGS. 18, 19, 23, and 24.

Figure 30:
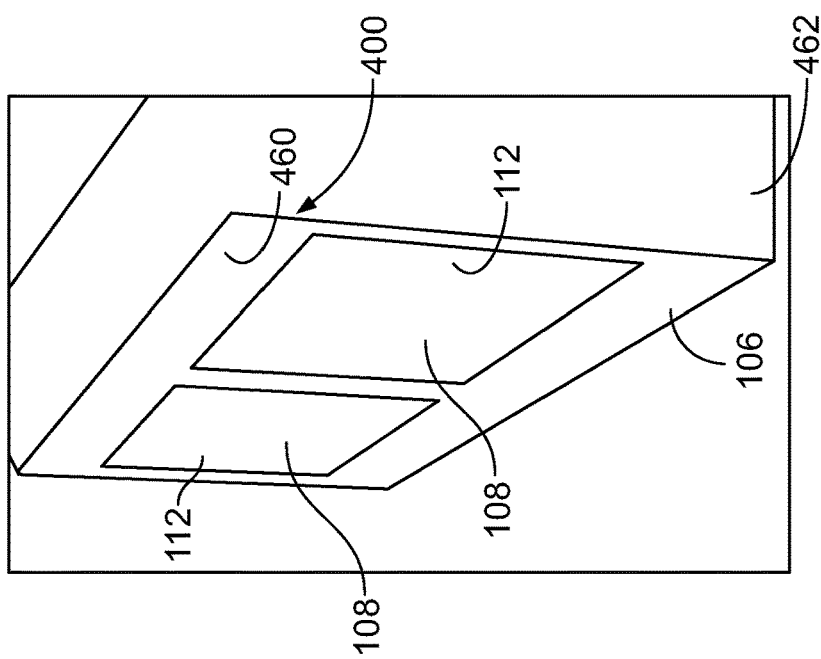
FIG. 30 illustrates a perspective front, lateral view of a module secured to a wall, according to an embodiment of the present disclosure.

FIG. 30 illustrates a perspective front, lateral view of the module 106 secured to the wall 440, according to an embodiment of the present disclosure. The sub-housing 400 may be secured to the wall 440 such that a front face 460, including the apertures 112, is flush with a front surface 462 of the wall 440.

Figure 31:
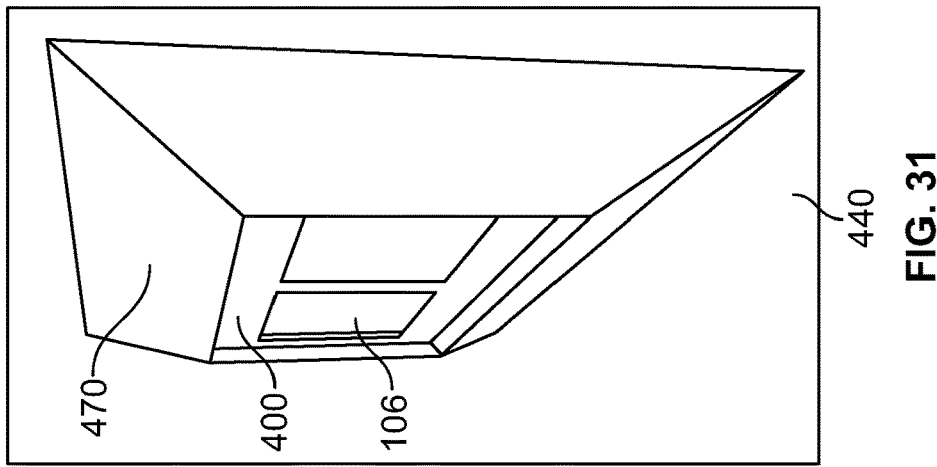
FIG. 31 illustrates a perspective front, lateral view of a module secured to a wall, according to an embodiment of the present disclosure.

FIG. 31 illustrates a perspective front, lateral view of the module 106 secured to the wall 440, according to an embodiment of the present disclosure. In this embodiment, the sub-housing 400 can be secured within a surrounding collar 470 that mounts the sub-housing 400 to the wall 440.

Figure 32:
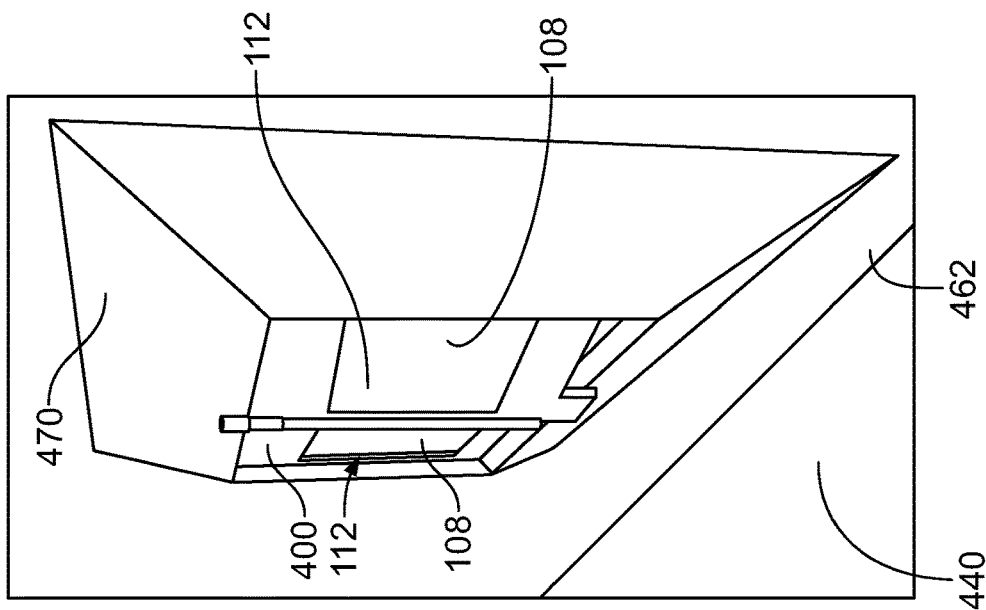
FIG. 32 illustrates a perspective front, lateral view of a module secured to a wall, according to an embodiment of the present disclosure.

FIG. 32 illustrates a perspective front, lateral view of the module 106 secured to the wall 440, according to an embodiment of the present disclosure. This embodiment is similar to that shown in FIG. 31, except that the apertures 112 may be angled (that is, not parallel) to the front surface 462 of the wall 440.

Figure 33:
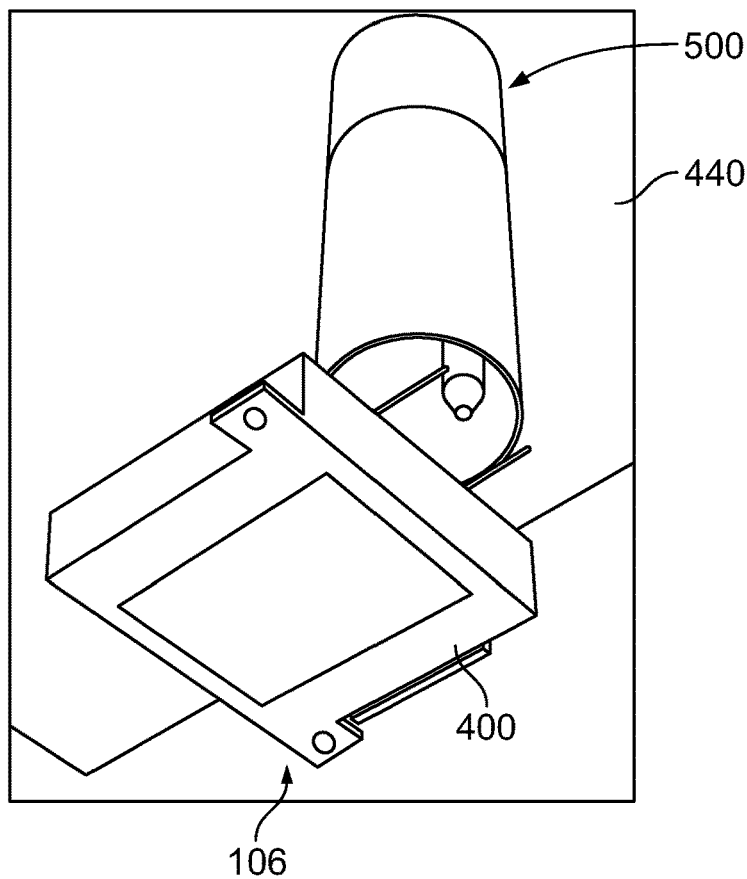
FIG. 33 illustrates a perspective front view of a module secured to a wall, according to an embodiment of the present disclosure.

FIG. 33 illustrates a perspective front view of the module 106 secured to the wall 440, according to an embodiment of the present disclosure. In this embodiment, a shielding shroud 500, such as a metal cylinder, is secured to and/or behind the wall 440. The power supply 402 (shown in FIG. 29, for example) is retained within the shielding shroud 500. In this embodiment, the shielding shroud 500 provides the EMI shielding for the power supply 402. Additional EMI shielding, such as in the form of a metal foil, may nor may not extend around the power supply 402 within the shielding shroud 500.

In at least one embodiment, the shielding shroud 500 is configured to fit into and be retained within an opening formed in the wall 440. As such, the shielding shroud 500 can be easily installed into the wall 440.

Figure 34:
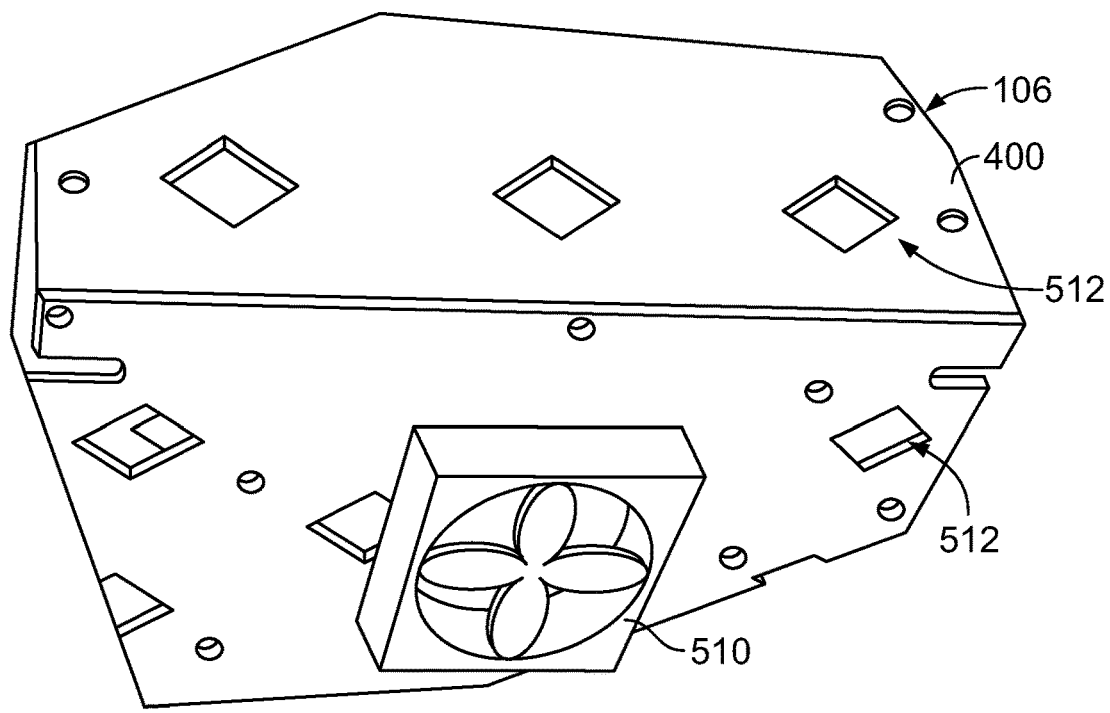
FIG. 34 illustrates a perspective rear view of a sub-housing of a module, according to an embodiment of the present disclosure.

FIG. 34 illustrates a perspective rear view of the sub-housing 400 of the module 106, according to an embodiment of the present disclosure. As shown, the sub-housing 400 may include a cooling fan 510 and a plurality of ventilation openings 512. The cooling fan 510 operates to cool the UV light emitters 108 during operation, and the ventilation openings 512 draw in cooling air and/or allow air within the sub-housing 400 to pass therethrough. The cooling fan 510 and the ventilation openings 512 may be used with any of the embodiments described herein. In embodiments in which an EMI shield covers portions of the sub-housing 400, the EMI shield does not cover the cooling fan 510 and the ventilation openings 512.

The ventilation openings 512 can be sized and shaped depending on EMI wavelength requirements. For example, in at least one embodiment, the ventilation openings 512 can be between 0.5"-1.0".

Figure 35:
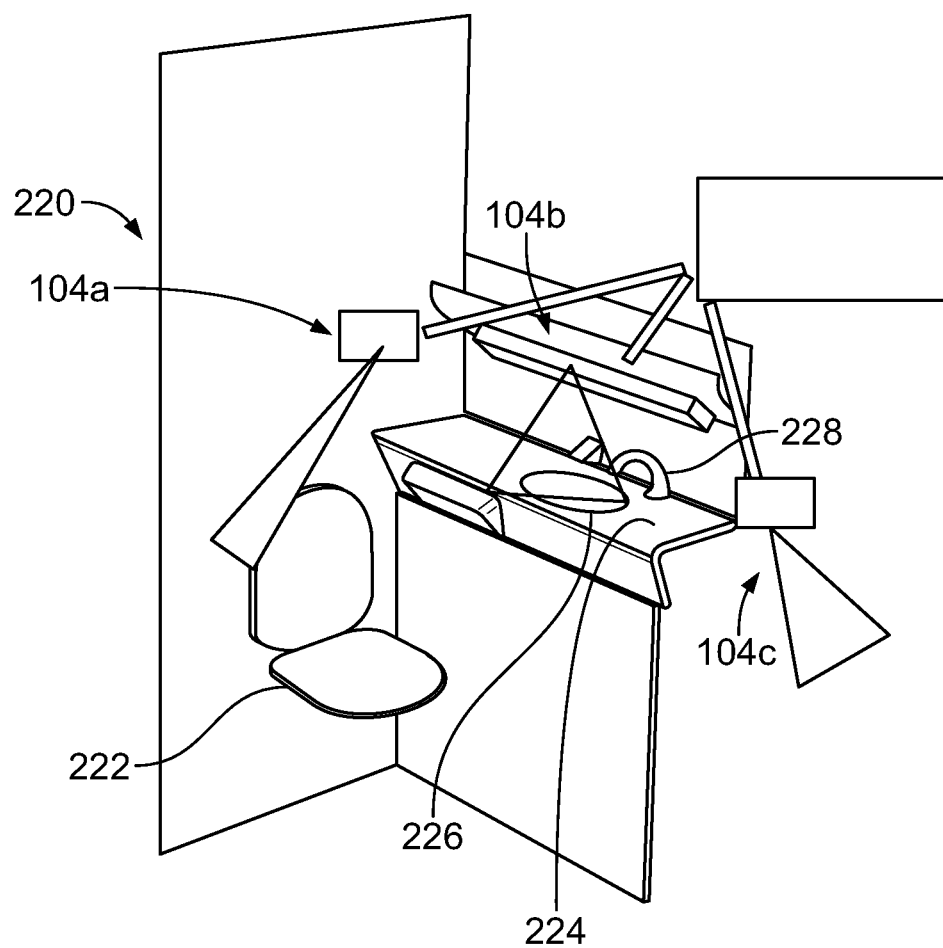
FIG. 35 illustrates a perspective internal view of a lavatory, according to an embodiment of the present disclosure.

FIG. 35 illustrates a perspective internal view of the lavatory 220, according to an embodiment of the present disclosure. The lavatory 220 can include a plurality of UV lamps, according to any of the embodiments described herein. For example, a first UV lamp 104*a* is configured to emit UV light onto a flush handle of the toilet 222. A second UV lamp 104*b* is configured to emit UV light onto the counter 224, including the sink 226 and the faucet 228. A third UV lamp 104*c* is configured to emit UV light onto a door handle, for example. The lavatory 220 can include more or less UV lamps than shown.

Figure 36:
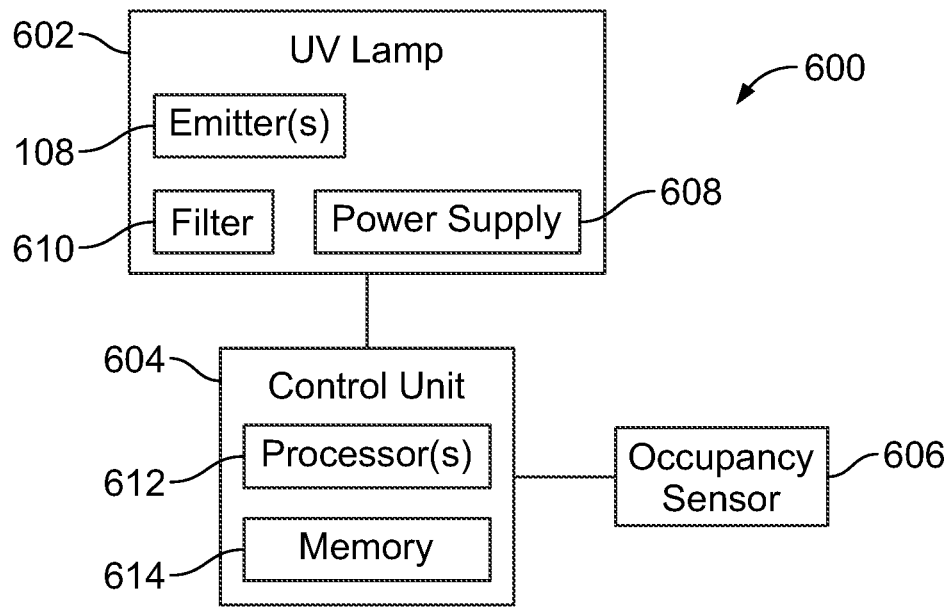
FIG. 36 illustrates a schematic block diagram of a sanitizing system for dynamically modulating an irradiance of ultraviolet (UV) light emitted into a space based on occupancy of the space, according to an embodiment of the present disclosure.

FIG. 36 illustrates a schematic block diagram of a sanitizing system 600 for dynamically modulating an irradiance of ultraviolet (UV) light emitted into a space based on occupancy of the space, according to an embodiment of the present disclosure. The sanitizing system 600 includes a UV lamp 602, a control unit 604, and a sensor (e.g., an occupancy sensor) 606.

The UV lamp 602 can be a contiguous UV lamp (that is, not formed from a plurality of modules) that has one or more UV light emitters 108, as described with respect to FIG. 1, for example. Optionally, the UV lamp 602 can be formed from multiple modules, as described herein. The UV lamp 608 includes a power supply 608. The power supply 608 provides electrical energy (e.g., current) to the one or more UV light emitters 108 to produce the UV light. The power supply 608 can include an electrical energy storage device, such as a battery (e.g., the battery 200 shown in FIG. 14), capacitors, and/or the like. The power supply 608 may also include a power cord (e.g., the power cord 202 in FIG. 14) for recharging the electrical energy storage device. In at least one other embodiment, the power supply 608 includes the power cord but lacks the electrical energy storage device, such that electrical energy received from an external power source is used to generate the UV light without storing electrical energy onboard the UV lamp 602. The power supply 608 may include or be connected with control circuitry and/or switching devices that can be controlled by the control unit 604 to dynamically modulate the power supplied to the UV light emitters 108 according to the operations and algorithms described herein.

The UV lamp 602 may also include a wavelength selective filter 610 that is configured to block emission of one or more wavelengths of the UV light into the target space. For example, the one or more UV light emitters 108 may be mounted within a housing of the UV lamp 602, and the wavelength selective filter 610 may be attached to the housing extending across a path of the UV light that is emitted from the one or more UV light emitters 108. The wavelength selective filter 610 may be utilized as a bandpass filter (which absorbs or blocks light at wavelengths both above and below a transmission region, referred to as a bandpass region), a bandstop filter (which only absorbs or blocks light at wavelengths within a designated bandstop region), a shortpass filter (which only absorbs or blocks light at wavelengths above the transmission region), or a longpass filter (which only absorbs or blocks light at wavelengths below the transmission region). The term transmission region broadly refers to the range of wavelengths of light permitted to pass through the wavelength selective filter according to the embodiments described herein. In one or more embodiments, the wavelength selective filter 610 may be designed as a bandpass filter that only allows transmission of a narrow range of UV wavelengths into the target space. The narrow wavelength range that is permitted to pass through the filter may be within the far UV and/or UV-C spectrum, such as a narrow range disposed between the bookends of 200 nm and 280 nm. The narrow wavelength range may have a width of less than 20 nm, such as less than 10 nm or even less than 6 nm. The narrow wavelength range may be centered around a designated wavelength, such as 222 nm.

The control unit 604 is operably connected (e.g., communicatively connected) to the UV lamp 602 and the occupancy sensor 606 via wired and/or wireless communication pathways. The control unit 604 generates control signals that control the operation of the UV lamp 602. The control signals may control the operation of the UV lamp 602 by controlling the presence and characteristics of electrical energy (e.g., voltage, current, phase, etc.) that is supplied to the UV light emitters 108. The control signals may be generated based at least part on sensor signals generated by the occupancy sensor 606 over time. As described above, the control unit 604 represents hardware circuitry that includes and/or is connected with one or more processors 612 (e.g., one or more microprocessors, integrated circuits, microcontrollers, field programmable gate arrays, etc.). The control unit 604 includes and/or is connected with a tangible and non-transitory computer-readable storage medium (e.g., memory) 614. For example, the memory 614 may store programmed instructions (e.g., software) that is executed by the one or more processors 612 to perform the operations of the control unit 604 described herein.

The occupancy sensor 606 is configured to monitor a target space and generate sensor signals over time indicative of an occupancy (e.g., occupancy status) of the target space. For example, the occupancy sensor 606 may use various working mechanisms to detect when one or more persons are present in the space. The occupancy sensor 606 may be a photoelectric sensor that emits an electromagnetic beam along an optical path and detects interruptions of the beam. The beam may be infrared (IR), laser, or the like. In another embodiment, the occupancy sensor 606 may be a pressure sensor that is disposed beneath the floor or within a seat to detect pressure exerted by the presence of a person in the space. The occupancy sensor 606 could be a camera with a processing unit that analyzes image data generated by the camera to deter the presence of people in the space. In another embodiment, the sensor 606 could be an acoustic sensor that detect sounds indicative of the presence of a person in the space, such as the sound of a person walking through the space, the sound of a person's voice, the sound of a door opening, or the like. In yet another embodiment, the occupancy sensor 606 could be an optical proximity and/or motion sensor that emits electromagnetic energy to detect the distance between the sensor 606 and an object in front of the sensor 606. The occupancy sensor 606 may be a contact sensor, such as a Hall-effect sensor, that is integrated with a door or a seat and detects when the door or seat moves. The occupancy sensor 606 generates sensor signals at fixed intervals or in response to detecting a changed condition in the space, and communicates the sensor signals to the control unit 604.

Figure 37:
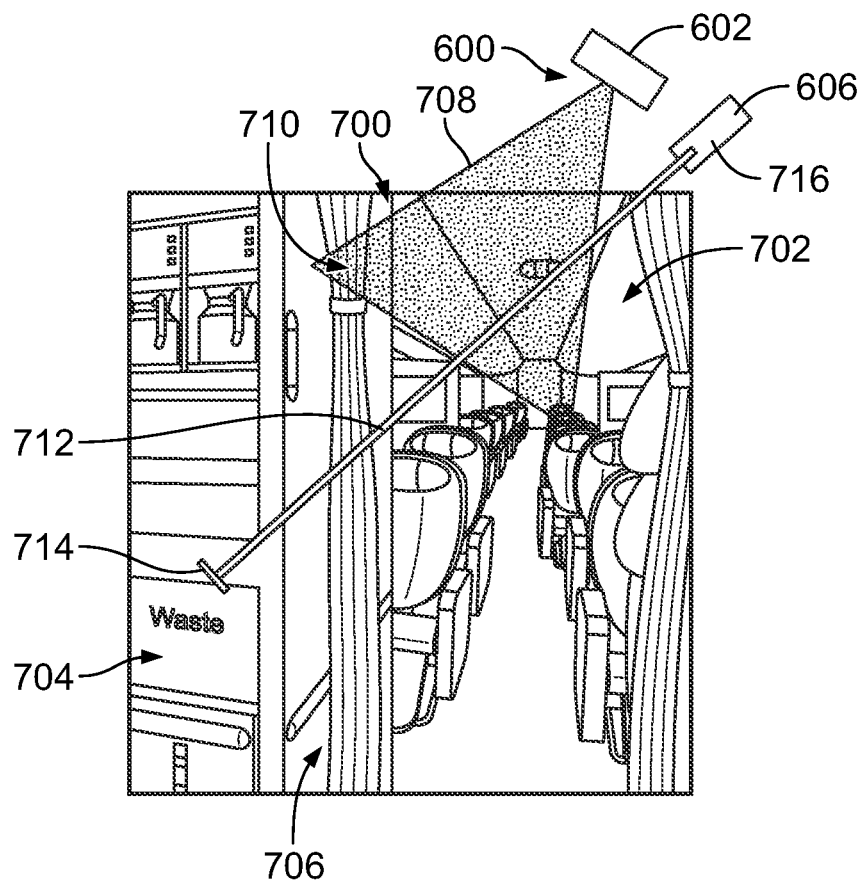
FIG. 37 illustrates a perspective internal view of the sanitizing system installed within an internal cabin of a vehicle, according to an embodiment of the present disclosure.

FIG. 37 illustrates a perspective internal view of the sanitizing system 600 installed within an internal cabin 700 of a vehicle according to an embodiment of the present disclosure. The internal cabin 700 represents at least one room. The internal cabin 700 includes a passenger section 702, a galley 704, and a cabin transition area or hallway 706 that connects the passenger section 702 to the galley 704. The vehicle may be a commercial aircraft, train, bus, marine vessel, or the like. The occupancy sensor 606 and the UV lamp 602 are fixedly mounted to walls within the internal cabin 700. In the illustrated embodiment, the occupancy sensor 606 is separate and spaced apart from the UV lamp 602. For example, the occupancy sensor 606 is disposed within the galley 704 and/or the transition area 706, and the UV lamp 602 is disposed within the transition area 706 and/or the passenger section 702. The UV lamp 602 emits UV light 708 into a target space 710. The target space 710 may be space within the cabin transition area 706 and/or a front area of the passenger section 702.

The UV lamp 602 is positioned and oriented to emit UV light towards one or more components within the internal cabin 700 to disinfect the one or more components. Although only one UV lamp 602 is shown in FIGS. 36 and 37, the sanitizing system 600 may include multiple UV lamps 602 that are spaced apart and mounted at different locations within the internal cabin 700 to emit UV light into different respective target spaces within the internal cabin 700 to disinfect different components within the internal cabin 700. The control unit 604 (shown in FIG. 36) may control each of the UV lamps 602 in the same way based on the determined occupancy of the internal cabin 700. For example, in response to the sensor signals from the occupancy sensor 606 indicating that a person is present, the control unit 604 may modulate all of the UV lamps 602 in the same manner over time, such as by gradually stepping down the irradiance of each of the UV lamps 602.

In the illustrated embodiment, the occupancy sensor 606 is a retro-reflective optical sensor that emits an energy beam 712 along an optical path across the target space 710. The retro-reflective optical sensor includes a reflector 714 that reflects the energy beam 712 back to the beam source 716. The occupancy sensor 606 is configured to detect occupancy of the internal cabin 700 based on an interruption in the optical path defined by the energy beam 712. For example, in FIG. 37, the beam source 716 is mounted relatively high and on the right side of the cabin transition area 706, and the reflector 714 is mounted relatively low and on the opposite, left side, such that the optical path extends diagonally across the cabin transition area 706 and experiences an interruption when a person walks through the cabin transition area 706. Based on the position and orientation of the beam source 716 and the reflector 714, the occupancy sensor 606 detects a change when an occupant crosses the optical path of the beam 712. By placing the occupancy sensor 606 along the relatively narrow cabin transition area 706 the single optical path can be used to detect any person entering or leaving the passenger section 702 through the transition area 706.

The control unit 604 (shown in FIG. 36) may be integrated with the occupancy sensor 606, integrated with the UV lamp 602, or remote from both the occupancy sensor 606 and the UV lamp 602. The control unit 604 is configured to receive the sensor signals generated by the occupancy sensor 606 and to modulate the irradiance of the UV light emitted by the UV lamp 602 (or lamps) over time based on the occupancy of the space.

In one or more embodiments, upon activation or reset of the control unit 604, the control unit 604 may initially assume that the internal cabin 700 is unoccupied. Upon determining, based on received sensor signals, that the optical path has been interrupted a single time, the control unit 604 determines that the space is occupied. If the optical path is interrupted a second time, the control unit 604 may not be able to decipher, merely from the single sensor 606, whether the same person that had crossed the optical path has crossed the optical path a second time to leave the space unoccupied or whether a second person has entered the space with the first person. In an embodiment, the control unit 604 may utilize sensor signals from at least a second occupancy sensor 606. The second occupancy sensor 606 in one embodiment may be the same type of retro-reflective optical sensor as the first, and may be disposed adjacent to the first such that the optical paths provided by the first and second sensors 606 may be interrupted in succession when a person enters or leaves the passenger section 702. Based on the relative positioning of the two optical sensors and the time delay between the interruptions, the control unit 604 can determine the direction of movement of the person, and can utilize the direction of movement to determine whether the area is occupied or unoccupied. For example, if the optical path of the first sensor 606 is interrupted before the optical path of the second sensor 606, and the second sensor 606 is closest to the passenger section 702, then the timing indicates that a person is walking towards the passenger section 702. Subsequently, if the optical path of the second sensor 606 is interrupted before the optical path of the first sensor 606, then that person likely left the passenger section 702. The control unit 604 may be configured to count the interruptions to determine the number of people that entered the passenger section 702, and can use that number to determine when the passenger section 702 is unoccupied. For example, if the interruptions in the optical paths indicate that four people have entered the passenger section 702, the control unit 604 determines that the passenger section 702 is occupied until subsequent interruptions indicate that four people have exited the passenger section 702.

In another embodiment, the second occupancy sensor 606 may be a different type of sensor than the first, retro-reflective optical sensor. For example, upon detecting the interruption in the optical path of the first occupancy sensor 606, the control unit 604 may activate a camera that generates image data of the passenger section 702, a pressure sensor within the passenger section 702, an acoustic sensor within the passenger section 702, an IR thermal sensor that monitors thermal signatures within the passenger section 702, and/or the like. The control unit 604 can combine the sensor signals received from the multiple different types of sensors to determine whether or not the space is occupied.

In an embodiment, in response to the sensor signals indicating that the space (e.g., the target space that is monitored) is unoccupied, the control unit 604 may operate the UV lamp 602 (or lamps) to emit UV light at a full irradiance level to disinfect one or more components. The full irradiance level may represent a full power setting or high power setting that is used to disinfect the components in the space when the space is unoccupied. If the space remains unoccupied, the control unit 604 may eventually deactivate the UV lamp 602 to cease emitting UV light at the full irradiance level after a predetermined time period for disinfection has elapsed. For example, deactivating the UV lamp 602 after the designated time period conserves energy. The designated time period represent the duration of a disinfection cycle, and may be on the order of minutes, such as 1 minute, 5 minutes, 10 minutes, 20 minutes, or the like. The designated time period for disinfection may be selected based on the irradiance of the UV light, the distance of the UV lamp 602 from the one or more components, and a desired dose of UV light to be applied to the one or more components. For example, the UV dose depends on the irradiance of the UV light, the proximity of the UV light, and the duration at which the UV light irradiates the one or more components, so the duration may be selected in order to achieve the desired dose without expending additional energy. As an example, the designated time period may be longer for a UV lamp that has a lower irradiance and/or is located farther from the target components being disinfected in order to provide a predetermined dose of UV light to the target components.

Although the components of the sanitizing system 600 in FIG. 37 are disposed along the cabin transition area between the galley and the passenger section, the sanitizing system 600 can be disposed at various other locations within the vehicle. For example, the sanitizing system 600 can be located within the lavatory 220 as shown in FIG. 35. In the lavatory example, the occupancy sensor 606 detects the occupancy of the lavatory, and the control unit 604 modulates the irradiance of the UV lamp 602 within the lavatory based on the sensor signals from the occupancy sensor 606.

In one or more other embodiments, the sanitizing system 600 may monitor and emit UV light into a target space that can be any space in or around a vehicle, building, structure, facility, or the like. The target space may be an enclosed area or room, but need not be enclosed. Non-limiting examples of buildings or facilities in which the sanitizing system 600 can be installed include theatres, concert venues, arenas, places of worship, banquet halls, commercial businesses, factories, hospitals, and/or the like. In embodiments in which the sanitizing system 600 is installed within vehicles, the vehicles can be passenger vehicles such as buses, trains, aircraft, marine vessels, or the like. In a commercial aircraft, the sanitizing system 600 can be located within areas of cargo, flight deck, lavatory, cabin, galleys, crew rest, assembly areas, and other areas in which individuals, passengers, flight crew, ground crew, and/or maintenance personnel may occupy or enter.

Figure 38:
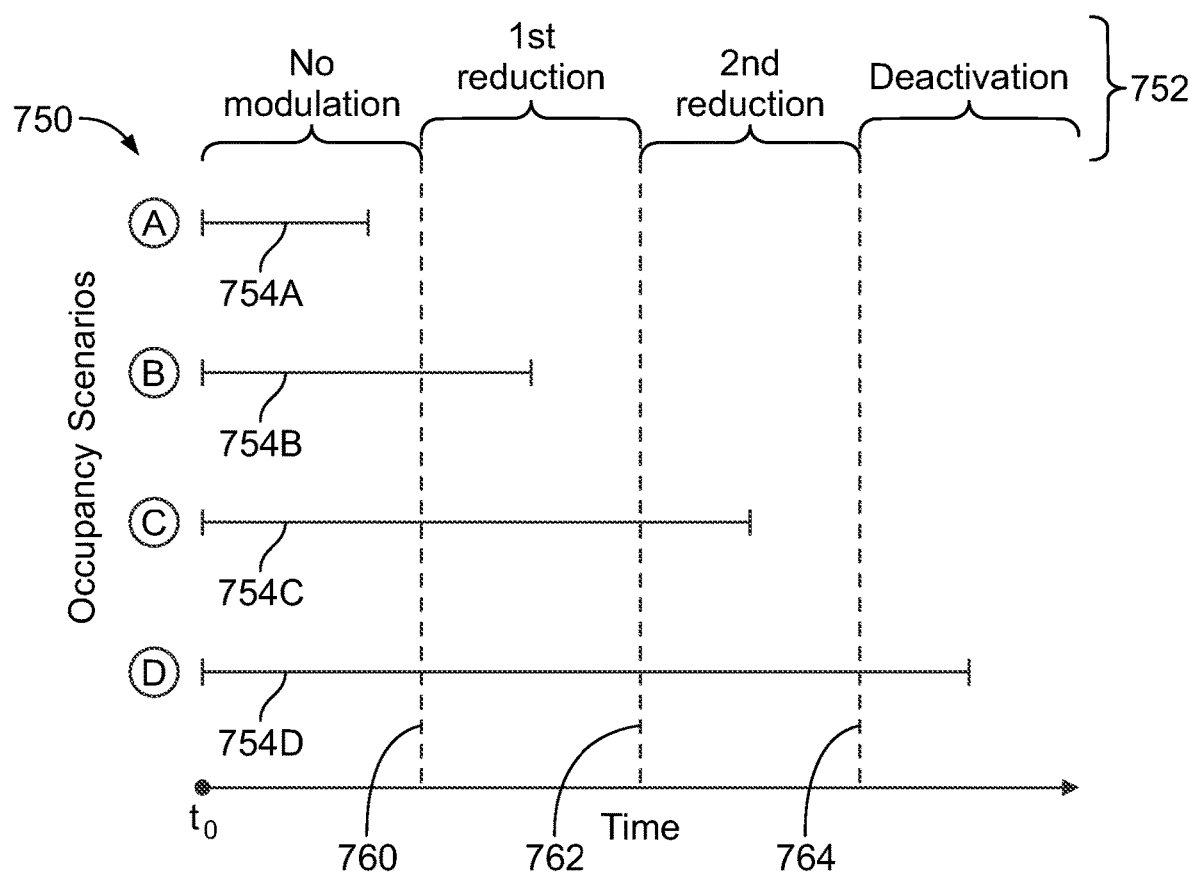
FIG. 38 is a diagram showing control operations of the sanitizing system according to multiple occupancy scenarios over time.

FIG. 38 is a diagram 750 showing control operations 752 of the sanitizing system 600 according to multiple occupancy scenarios over time. The occupancy scenarios are labeled A, B, C, and D. In each scenario, occupancy of a target space monitored by the occupancy sensor 606 (or sensors) is detected at time $t_0$. Each scenario includes a respective bar 754A, 754B, 754C, 754D that represents an occupancy duration (or occupancy period) in which the target space is occupied, starting at time $t_0$. As shown, the scenarios A-D have increasing occupancy durations such that the occupancy duration in scenario A is shortest and the occupancy duration in scenario D is longest. The occupancy duration represents the time from initial detection of occupancy of the space to the time at which it is determined that the space is unoccupied. For example, if the sanitizing system 600 detects that three people have entered the space during a common time period, the occupancy duration does not end until all three people have exited the space and no other people have entered the space.

The control operations 752 represent non-limiting, example responses of the control unit 604 to the different occupancy durations of the four scenarios. The control operations 752 and any other responsive actions undertaken by the control unit 604 may be based on programmed instructions embedded in the control logic of the processors 612 or stored in the memory 614. The control operations 752 indicate how the control unit 604 modulates the irradiance of the UV lamp 602 based on the occupancy. In each of the scenarios A-D, it is assumed that the UV lamp 602 is operating at the full irradiance level prior to the initial occupancy detection at time $t_0$. In the illustrated embodiment, the control unit 604 may compare the monitored occupancy to multiple threshold time periods, which may be predetermined and stored in the memory 614. The diagram 750 shows a first threshold time period 760, a second threshold time period 762, and a third threshold time period 764, which are indicated by dashed lines that intersect the timeline. Each of the threshold time periods 760, 762, 764 extends from time $t_0$ to the time associated with the respective dashed line, such that the first threshold time period 760 is shortest and the third threshold time period 764 is longest.

In scenario A, it is determined that the target space is occupied, but the occupancy period 754A ends prior to the end of the first threshold time period 760. For example, a person may walk into the target space and immediate exit the target space, such that the occupation is transient. The occupancy duration in scenario A may be only one or a few seconds. For example, the first threshold time period 760 may be a value within a range from 1 second to 10 seconds, such as two seconds, three seconds, four seconds, five seconds, six seconds, or the like, and it is shown that the occupancy duration in scenario A is less than the first threshold time period 760. In an embodiment, in response to determining a situation as shown in scenario A, in which the target space is occupied for a period of time that does not exceed the first threshold time period 760, the control unit 604 (e.g., the one or more processors 612 thereof) is configured to operate the UV lamp 602 to emit the UV light at the full irradiance level. For example, at such a short or transient occupation, the control unit 604 does not even adjust the power output of the UV lamp 602 because such a transient exposure to the UV light would not pose any risk of harm to the occupant or occupants within the space.

In scenario B, the occupancy period 754B exceeds the first threshold time period 760 but ends prior to the second threshold time period 762. In an embodiment, once the control unit 604 determines, based on the sensor signals, that the occupancy exceeds the first threshold time period 706, the control unit 604 controls the UV lamp 602 to reduce the irradiance of the UV light to a reduced irradiance level (e.g., a first reduced irradiance level) while continuing to emit the UV light into the target space. The control unit 604 steps down the irradiance of the UV lamp upon crossing the first threshold time period 760. In a non-limiting example, the full irradiance level may have an irradiance of 2 mW/cm$^2$, and the first reduced irradiance level may have an irradiance of 1 mW/cm$^2$. The first reduced irradiance level may be greater than the irradiance provided by a nominal lower power setting. Optionally, after determining that the space is once again unoccupied at the end of the occupancy period 754B, the control unit 604 may increase (e.g., step up) the irradiance of the UV lamp 602 to the full irradiance level to continue disinfecting the components in the space at the desired irradiance level. The UV lamp 602 operating at the reduced irradiance level not only reduces the energy or intensity of the UV light that could impinge on an occupant relative to the full irradiance level, but also reduces the energy consumption (e.g., power draw) of the UV lamp 602. By reducing the irradiance level, the UV lamp 602 could be operated for a longer period of time between charging (e.g., charge cycles) than if the UV lamp 602 is only operated at the full irradiance level.

The occupancy period 754C in scenario C exceeds the first and the second threshold time periods 760, 762, but ends prior to the third threshold time period 764. In response to determining that the occupancy period 754C exceeds the second threshold time period 762, the control unit 604 controls the UV lamp 602 to reduce the irradiance of the UV light further to a second reduced irradiance level, while continuing to emit the UV light into the target space. The first reduced irradiance level has greater power (e.g., greater irradiance) than the second reduced irradiance level. If the first irradiance level is the 1 mW/cm$^2$ as described in the example, above, the second irradiance level is less than 1 mW/cm$^2$, such as 0.5 mW/cm$^2$. The second threshold time period 762 may be a value within a range from three seconds to 20 seconds, such as five seconds, 10 seconds, or the like. Optionally, after determining that the space is unoccupied at the end of the occupancy period 754C, the control unit 604 may increase (e.g., step up) the irradiance of the UV lamp 602 to the full irradiance level to continue disinfecting the components in the space at the desired irradiance level.

In scenario D, the occupancy period 754D exceeds the first, second, and third threshold time periods 760, 762, 764. In response to determining, based on the sensor signals, that the occupancy period 754D exceeds the third threshold time period 764, the control unit 604 deactivates the UV lamp 602 to cease the UV lamp 602 from emitting UV light. For example, once the occupation persists longer than the third threshold time period 764, the control unit 604 turns off the UV lamp 602 entirely to halt the disinfection process. In another embodiment, instead of deactivating the UV lamp 602, the control unit 604 may step down the irradiance of the UV light again (e.g., to a level below the second reduced irradiance level) by selecting a nominal, lowest power setting for the UV lamp 602. The third threshold time period 764 may be a value within a range from 10 seconds to 40 seconds, such as 15 seconds, 20 seconds, or the like. Optionally, after determining that the space is unoccupied at the end of the occupancy period 754D, the control unit 604 may increase (e.g., step up) the irradiance of the UV lamp 602 to the full irradiance level to continue disinfecting the components in the space at the desired irradiance level.

The examples described with reference to the diagram 750 indicate that the control unit 604 may module the irradiance of the UV light based on a detected occupancy of the target space by initially postponing any irradiance adjustment, then stepping down the irradiance one or more times before eventually deactivating the UV lamp (or operating the UV lamp at a nominal, low power settings) as the occupancy persists. The number of step-downs may vary for different embodiments. For example, although two step-downs are described in FIG. 38, in another embodiment the control unit 604 may only utilize one irradiance step-down before deactivating the UV lamp 602. In such an embodiment, either the first or second threshold time period 760, 762 may be omitted, and the third threshold time period 764 may represent a second threshold time period. The terms "first", "second", and "third" are used herein merely for identifying and differentiating the multiple thresholds that can be used by the sanitizing system 600. In another embodiment, the control unit 604 may utilize three or more irradiance step-downs before deactivating the UV lamp 602.

In one or more other embodiments, instead of discrete step-downs in UV irradiance upon occupation persisting beyond successive time thresholds, the control unit 604 may more fluidly control the UV lamp 602 to gradually reduce the irradiance over time at a designated reduction rate. For example, upon detecting that the space is occupied, the control unit 604 may control the UV lamp 602 to continuously decrease the irradiance or power output over time at the designated reduction rate until the UV lamp 602 eventually turns off, the irradiance reaches the nominal low power setting, or it is determined that the space is no longer occupied, whichever occurs first. Alternatively, instead of beginning the sliding-scale reduction of the UV irradiance immediately upon occupation, the control unit 604 may delay the irradiance reduction until after the occupation period surpasses the first threshold time period 760, as shown in FIG. 38.

In one or more embodiments, the threshold time periods and/or the irradiation levels of the UV light utilized for the control operations described above may be determined based at least in part on the wavelength or wavelength range of the UV light emitted by the UV lamp 602. In a non-limiting example, the UV lamp 602 may emit UV light at 222 nm, or at a narrow wavelength range that includes 222 nm, such as a range from 200 nm to 225 nm. This wavelength and/or narrow wavelength range may be associated with a threshold limit value (TLV), according to ACGIH.

The wavelength or narrow wavelength range of the UV light emitted from the UV lamp 602 may be controlled by the wavelength selective filter 610 (shown in FIG. 36). For example, the wavelength selective filter 610 may be specifically designed and constructed to only emit a predetermined wavelength or narrow wavelength range. In an embodiment, once the wavelength or narrow wavelength range of UV light from the UV lamp 602 is known, the control unit 604 can consult a chart to determine the TLV of the UV light. Then, the control unit 604 select other parameters for the control operations, such as the values of the reduced irradiance levels, based on the TLV of the UV light to avoid providing a germicidal dose that exceeds the TLV into an occupied space.

The TLV of the wavelength and/or narrow wavelength range according to an embodiment is sufficiently large to enable a germicidal useful dose of UV light to be delivered to an area while that area is occupied. For example, the TLV may be 23 mJ/cm$^2$, and the germicidal dose could be in a range from 2 mJ/cm$^2$ to 20 mJ/cm$^2$, such that the germicidal dose does not exceed the TLV. Controlling the wavelength of the UV light that is emitted to have a relatively high TLV that exceeds the germicidal dose allows for a useful level of irradiance to continue in a nominally occupied space. In a non-limiting example, operating a 222 nm UV lamp to illuminate an area at a low power irradiance level of 1 mW could allow for about 23 seconds of exposure before exceeding the maximum allowable exposure level. Operating the same UV lamp at a high (or full) power irradiance level of 10 mW could allow for 2.3 seconds of exposure before exceeding the maximum allowable exposure level. As a result, the control unit 604 may set the first threshold time period 760 in FIG. 38 to be a value less than 2.3 seconds, such as 2 seconds, to avoid exceeding the allowable UV exposure level or dose. By understanding the exposure levels of the UV light, the sanitizing system 600 can provide for continued emission of UV light at a fairly high power into the space after detecting that the space is occupied, although only for a short, transient amount of time. By initially postponing the irradiance reduction, the sanitizing system 600 can provide enhanced disinfection of a nominally occupied area relative to immediately deactivating the UV upon detecting occupancy. If the UV lamp is stepped down, due to persistent occupation of the space, to the low power irradiance level of 1 mW, a subsequent threshold time period may be set to a value less than 23 seconds, such as 20 seconds, to avoid exceeding the allowable UV exposure level or dose. It is noted that the TLV value of 23 mJ/cm$^2$ for 222 nm UV light is provided for example, and the actual TLV value of 222 nm UV light may be different, such as greater than 23 mJ/cm$^2$.

The control unit 604 according to one or more embodiments may determine periodic occupancy trends for the target space, and may utilize the periodic occupancy trends to modulate the irradiance of the UV light that is emitted by the UV lamp 602 over time. Unlike the control operations 752 shown and described with reference to FIG. 38 that are based on real-time occupancy data of the target space, the control unit 604 may also analyze historical occupancy data associated with the target space and/or similar spaces in similar, but different, vehicles or buildings. For example, the historical occupancy data may include all of the sensor signals generated by the occupancy sensor or sensors 606 that monitor the target space over a previous extended time period, such as the prior month or year. The one or more processors 612 of the control unit 604 may analyze the historical occupancy data to determine the periodic occupancy trends for the target space. The periodic occupancy trends may indicate cyclic occupancy patterns within the target space, including a level of deviation from the patterns. The periodic occupancy trends may identify certain time periods during each day or week in which the target space is typically unoccupied and other time periods during the day or week in which the target space is typically occupied. For example, on Mondays, the target space is typically unoccupied for an hour from 7 AM to 8 AM. The periodic occupancy trends may also indicate the density of occupancy, such as the expected amount of people within the target space at different times of the day or week.

In an embodiment, at least one of the one or more processors 612 may represent or include a prediction module or feature that utilizes data analysis, machine learning, and/or artificial intelligence (AI) to generate the periodic occupancy trends. By analyzing the historical data, the prediction module may "learn" how the target space is typically occupied, and then modulate the irradiance of the UV light based on the learned occupancy trends. Optionally, the prediction module may correlate the historical occupancy data of the target space with historical (e.g., past) schedules, such as trip schedules in the case of the space being within a commercial vehicle. The prediction module can "learn" or identify how the occupancy of the space correlates with the schedules. For example, if a trip is scheduled to begin at 6 AM and the vehicle has been stationary for at least a few hours, the data may indicate that the space is occupied by a cleaning crew one hour prior to the departure time, and then is unoccupied for a certain interval of time until the trip crew occupies the space 30 minutes prior to the departure. Using this information, the control unit 604 can schedule a disinfection process by the UV lamp 602 to occur within the interval between the cleaning crew exiting the space and the trip crew entering the space. Depending on the duration of this interval within the periodic occupancy trends, the control unit 604 may adjust one or more settings of the disinfection process. For example, if the interval is relatively short, then the control unit 604 can increase the power to the UV lamp to increase the full irradiance level of the UV light. As a result of the increased irradiance, the control unit 604 may also shorten one or more of the threshold time periods 760, 762, 764 in FIG. 38 to avoid excess UV exposure to any persons that enter the space during the disinfection process. Such adjustment of the disinfection start time, duration, UV irradiance, and threshold time periods based on the periodic occupancy trends can be used to provide efficient disinfection of the components within the target space and ensure safety of any person that enters the target space during the disinfection process.

Figure 39:
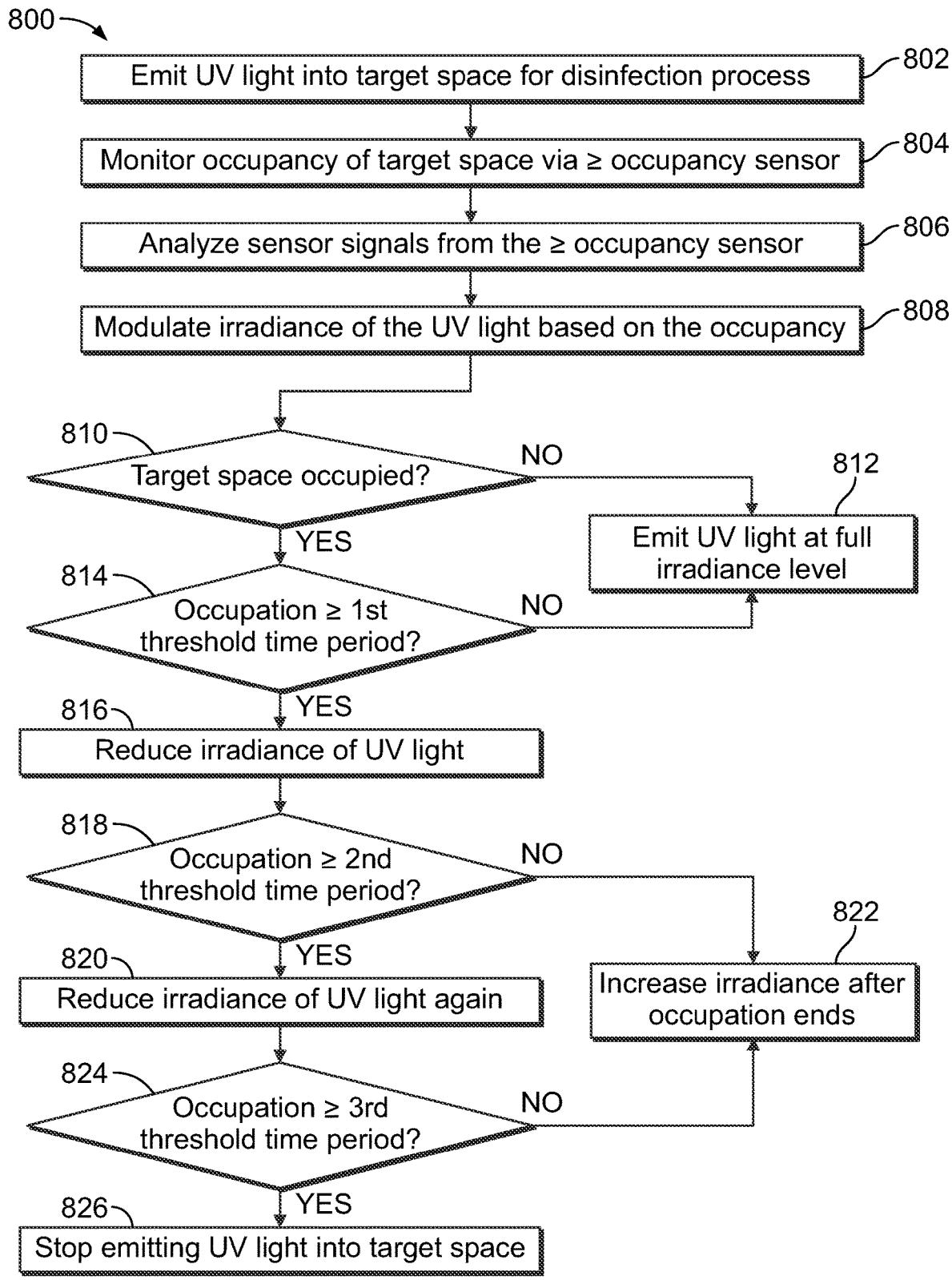
FIG. 39 illustrates a flow chart of a sanitizing method, according to an embodiment of the present disclosure.

FIG. 39 illustrates a flow chart 800 of a sanitizing method according to an embodiment of the present disclosure. Referring to FIGS. 36 through 38, the method begins at 802, at which the UV light is emitted into a target space for a disinfection process. The UV light is directed towards one or more components in the target space to neutralize pathogens on the components and/or in the air. The UV light is generated by at least one UV lamp 602. The target space may be a region within an enclosed area or room, such as of a commercial vehicle or a building.

At 804, the target space is monitored via one or more occupancy sensors 606 that are configured to generate sensor signals over time indicative of an occupancy of the target space. At 806, the sensor signals from the one or more occupancy sensors 606 are analyzed via a control unit 604 that comprises one or more processors 612. At 808, an irradiance of the UV light that is emitted into the target space is modulated, over time, based on the occupancy of the target space. The control unit 604 may control the modulation of the UV light that is emitted by the UV lamp 602 by generating control signals that are communicated to the UV lamp 602.

The following steps and operations of the method describe how the irradiance of the UV light may be monitored. At 810, it is determined, by the control unit 604, whether the target space is occupied. If the target space is determined to be unoccupied, the method proceeds to 812, and the UV light is emitted into the target space at a full irradiance level, which may represent a full power or high power setting. If, on the other hand, the target space is determined to be occupied at 810, then flow proceeds to 814 where a determination is made, by the control unit 604, whether the occupation of the target space persists for at least as long as a first threshold time period 760. If not, then flow returns to 812 and the UV light continues to be emitted at the full irradiance level. On the other hand, if the occupation persists for at least as the first threshold time period 760, then the method proceeds to 816. At 816, the irradiance of the UV light is reduced, such as to a first reduced irradiance level.

At 818, it is determined, by the control unit 604, whether the occupation of the target space persists for at least as long as a second threshold time period 762 (which is longer than the first threshold time period 760). If not, once the occupation is determined to be over, such that the space is once again unoccupied, the irradiance of the UV light is increased at 822. The UV irradiance may be increased back to the full irradiance level. If, on the other hand, the occupation persists for at least as long as the second threshold time period 762, the method proceeds to 820 and the irradiance of the UV light is reduced again (e.g., a second time) to an irradiance level below the previous irradiance level. Even at the second reduced irradiance level, the UV light may have an irradiance that is greater than a nominal or lower limit irradiance level. From 820 the method proceeds to 824 and it is determined, by the control unit 604, whether the occupation of the target space persists for at least as long as a third threshold time period 764 (which is longer than the second threshold time period 762). If not, once the occupation is determined to be over, such that the space is once again unoccupied, the irradiance of the UV light is increased at 822. If, on the other hand, the occupation persists for at least as long as the third threshold time period 764, the method proceeds to 826 and the UV light is stopped from further emission into the target space. For example, the control unit 604 may deactivate or turn off the UV lamp 602.

Figure 40:
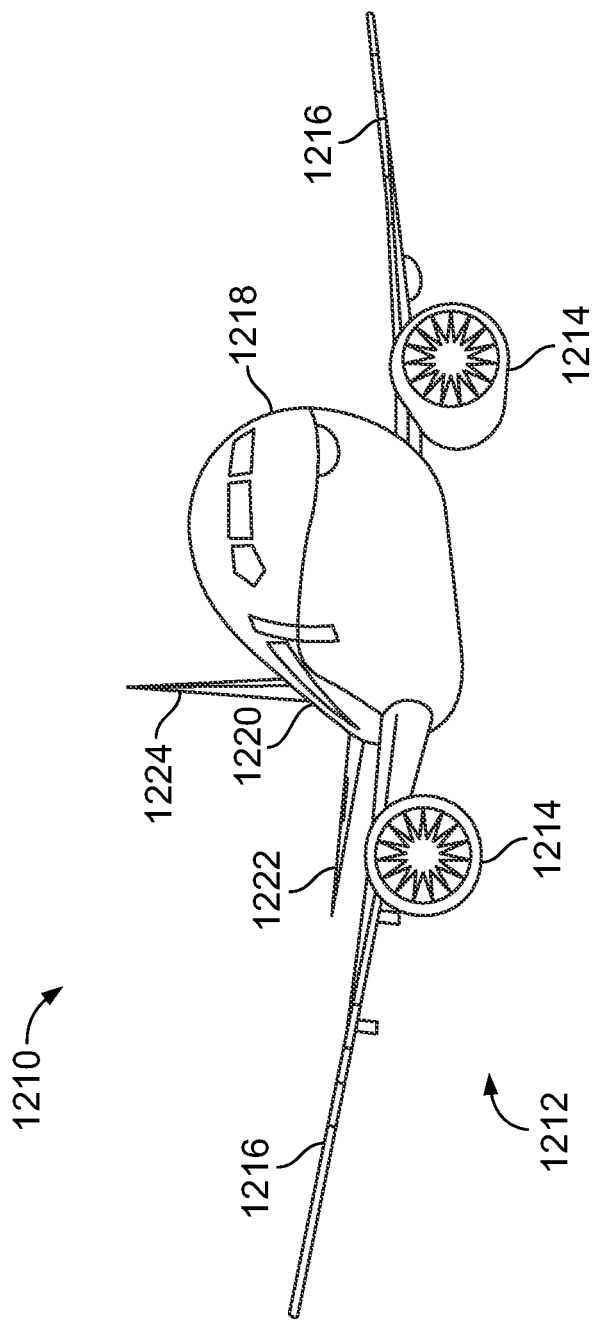
FIG. 40 illustrates a perspective front view of an aircraft, according to an embodiment of the present disclosure.

FIG. 40 illustrates a perspective front view of an aircraft 1210, according to an embodiment of the present disclosure. The aircraft 1210 includes a propulsion system 1212 that includes engines 1214, for example. Optionally, the propulsion system 1212 may include more engines 1214 than shown. The engines 1214 are carried by wings 1216 of the aircraft 1210. In other embodiments, the engines 1214 may be carried by a fuselage 1218 and/or an empennage 1220. The empennage 1220 may also support horizontal stabilizers 1222 and a vertical stabilizer 1224.

The fuselage 1218 of the aircraft 1210 defines an internal cabin 1230, which includes a flight deck or cockpit, one or more work sections (for example, galleys, personnel carry-on baggage areas, and the like), one or more passenger sections (for example, first class, business class, and coach sections), one or more lavatories, and/or the like.

Embodiments of the present disclosure are used to disinfect various components within the internal cabin 1230. Alternatively, instead of an aircraft, embodiments of the present disclosure may be used with various other vehicles, such as automobiles, buses, locomotives and train cars, watercraft, and the like. Further, embodiments of the present disclosure may be used with respect to fixed structures, such as commercial and residential buildings.

Figure 41A:
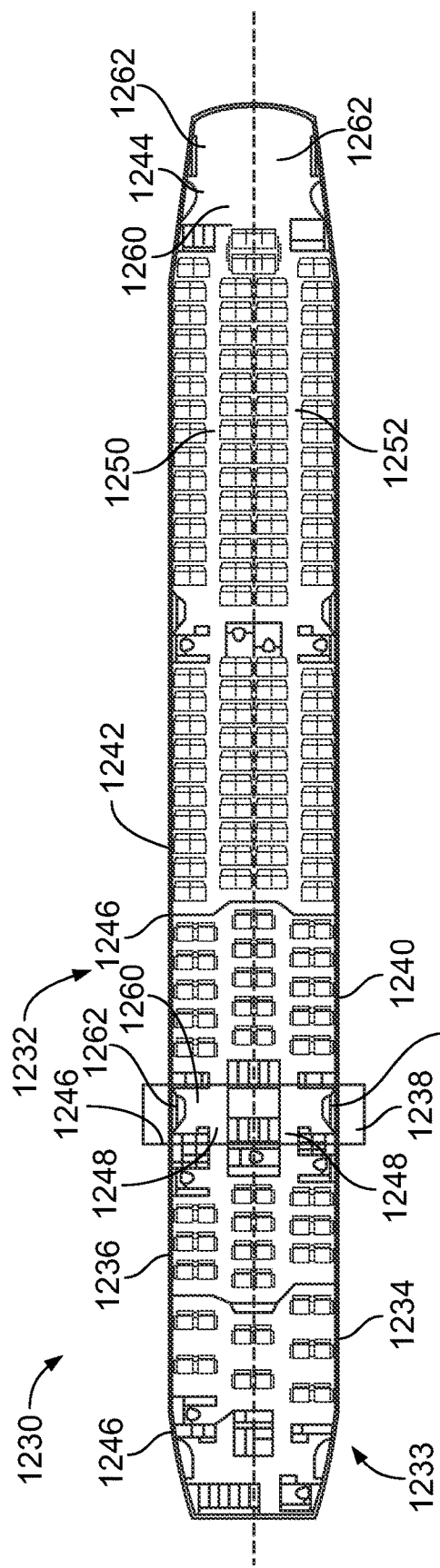
FIG. 41A illustrates a top plan view of an internal cabin of an aircraft, according to an embodiment of the present disclosure.

FIG. 41A illustrates a top plan view of an internal cabin 1230 of an aircraft, according to an embodiment of the present disclosure. The internal cabin 1230 may be within the fuselage 1232 of the aircraft, such as the fuselage 1218 of FIG. 40. For example, one or more fuselage walls may define the internal cabin 1230. The internal cabin 1230 includes multiple sections, including a front section 1233, a first class section 1234, a business class section 1236, a front galley station 1238, an expanded economy or coach section 1240, a standard economy of coach section 1242, and an aft section 1244, which may include multiple lavatories and galley stations. It is to be understood that the internal cabin 1230 may include more or less sections than shown. For example, the internal cabin 1230 may not include a first class section, and may include more or less galley stations than shown. Each of the sections may be separated by a cabin transition area 1246, which may include class divider assemblies between aisles 1248.

As shown in FIG. 41A, the internal cabin 1230 includes two aisles 1250 and 1252 that lead to the aft section 1244. Optionally, the internal cabin 1230 may have less or more aisles than shown. For example, the internal cabin 1230 may include a single aisle that extends through the center of the internal cabin 1230 that leads to the aft section 1244.

The aisles 1248, 1250, and 1252 extend to egress paths or door passageways 1260. Exit doors 1262 are located at ends of the egress paths 1260. The egress paths 1260 may be perpendicular to the aisles 1248, 1250, and 1252. The internal cabin 1230 may include more egress paths 1260 at different locations than shown. Embodiments of the present disclosure shown and described with respect to FIGS. 1-39 may be used to sanitize various structures within the internal cabin 1230, such as passenger seats, monuments, stowage bin assemblies, components on and within lavatories, galley equipment and components, and/or the like.

Figure 41B:
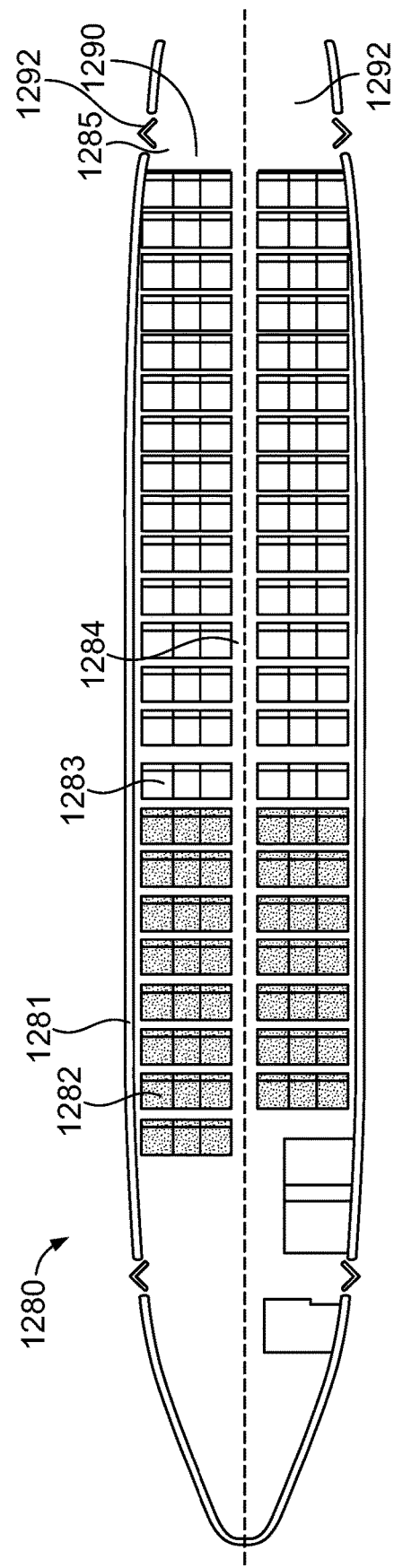
FIG. 41B illustrates a top plan view of an internal cabin of an aircraft, according to an embodiment of the present disclosure.

FIG. 41B illustrates a top plan view of an internal cabin 1280 of an aircraft, according to an embodiment of the present disclosure. The internal cabin 1280 is an example of the internal cabin 1230 shown in FIG. 41A and the internal cabin 700 shown in FIG. 37. The internal cabin 1280 may be within a fuselage 1281 of the aircraft. For example, one or more fuselage walls may define the internal cabin 1280. The internal cabin 1280 includes multiple sections, including a main cabin 1282 having passenger seats 1283, and an aft section 1285 behind the main cabin 1282. It is to be understood that the internal cabin 1280 may include more or less sections than shown.

The internal cabin 1280 may include a single aisle 1284 that leads to the aft section 1285. The single aisle 1284 may extend through the center of the internal cabin 1280 that leads to the aft section 1285. For example, the single aisle 1284 may be coaxially aligned with a central longitudinal plane of the internal cabin 1280.

The aisle 1284 extends to an egress path or door passageway 1290. Exit doors 1292 are located at ends of the egress path 1290. The egress path 1290 may be perpendicular to the aisle 1284. The internal cabin 1280 may include more egress paths than shown. Embodiments of the present disclosure shown and described with respect to FIGS. 1-39 may be used to sanitize various structures within the internal cabin 1230, such as passenger seats, monuments, stowage bin assemblies, components on and within lavatories, galley equipment and components, and/or the like.

Figure 42:
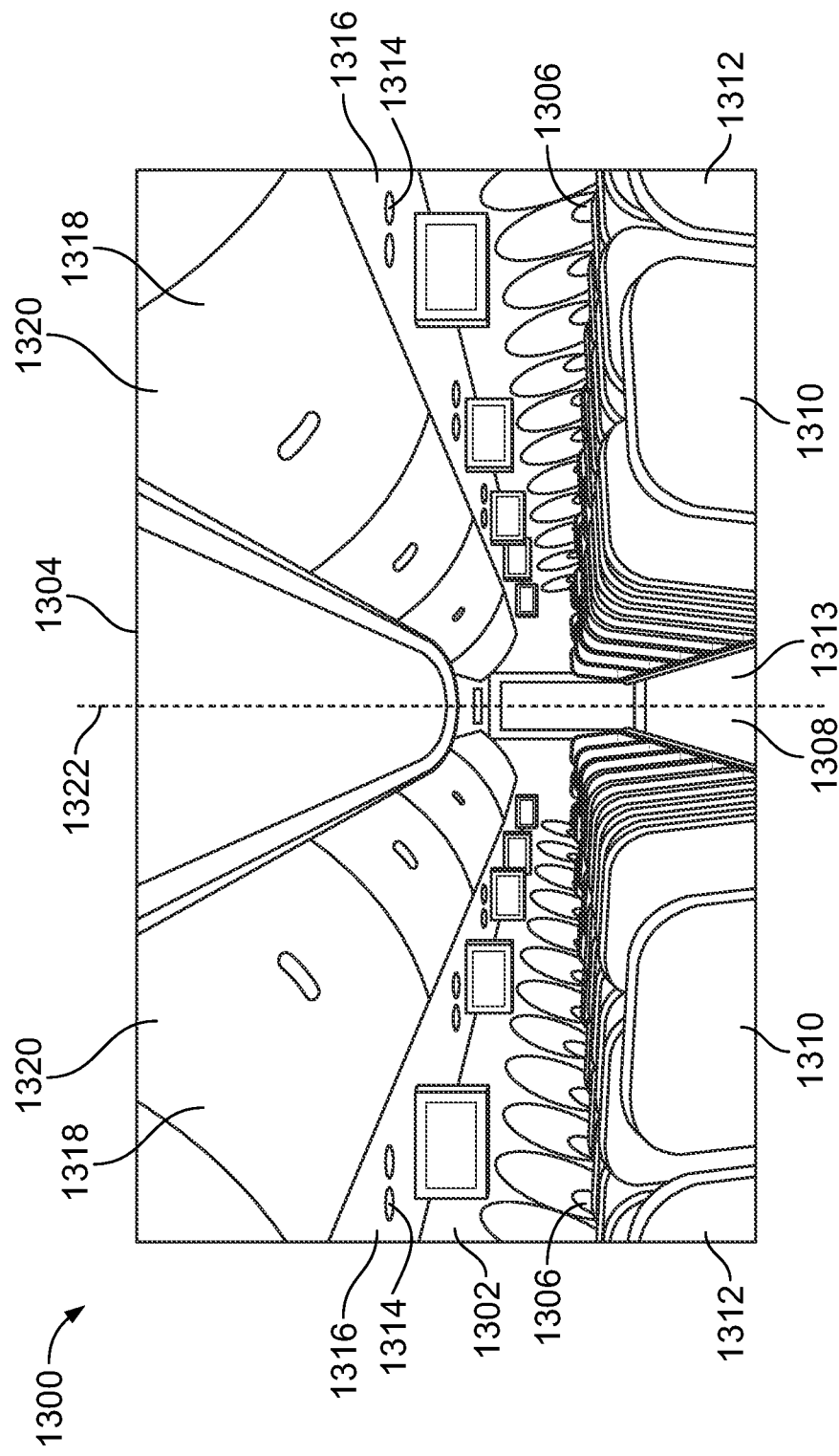
FIG. 42 illustrates a perspective interior view of an internal cabin of an aircraft, according to an embodiment of the present disclosure.

FIG. 42 illustrates a perspective interior view of an internal cabin 1300 of an aircraft, according to an embodiment of the present disclosure. The internal cabin 1300 includes outboard walls 1302 connected to a ceiling 1304. Windows 1306 may be formed within the outboard walls 1302. A floor 1308 supports rows of seats 1310. As shown in FIG. 42, a row 1312 may include two seats 1310 on either side of an aisle 1313. However, the row 1312 may include more or less seats 1310 than shown. Additionally, the internal cabin 1300 may include more aisles than shown.

Passenger service units (PSUs) 1314 are secured between an outboard wall 1302 and the ceiling 1304 on either side of the aisle 1313. The PSUs 1314 extend between a front end and rear end of the internal cabin 1300. For example, a PSU 1314 may be positioned over each seat 1310 within a row 1312. Each PSU 1314 may include a housing 1316 that generally contains vents, reading lights, an oxygen bag drop panel, an attendant request button, and other such controls over each seat 1310 (or groups of seats) within a row 1312.

Overhead stowage bin assemblies 1318 are secured to the ceiling 1304 and/or the outboard wall 1302 above and inboard from the PSU 1314 on either side of the aisle 1313. The overhead stowage bin assemblies 1318 are secured over the seats 1310. The overhead stowage bin assemblies 1318 extend between the front and rear end of the internal cabin 1300. Each stowage bin assembly 1318 may include a pivot bin or bucket 1320 pivotally secured to a strongback (hidden from view in FIG. 42). The overhead stowage bin assemblies 1318 may be positioned above and inboard from lower surfaces of the PSUs 1314. The overhead stowage bin assemblies 1318 are configured to be pivoted open in order to receive passenger carry-on baggage and personal items, for example.

As used herein, the term "outboard" means a position that is further away from a central longitudinal plane 1322 of the internal cabin 1300 as compared to another component. The term "inboard" means a position that is closer to the central longitudinal plane 1322 of the internal cabin 1300 as compared to another component. For example, a lower surface of a PSU 1314 may be outboard in relation to a stowage bin assembly 1318.

Embodiments of the present disclosure shown and described with respect to FIGS. 1-39 may be used to sanitize various structures shown within the internal cabin 1300.

As described herein, certain embodiments of the present disclosure provide systems and methods that allow for efficient disinfection of a target space or room even when the space or room is occasionally occupied. Further, certain embodiments of the present disclosure provide systems and methods that modulate the irradiance of emitted UV light to ensure that the UV dosage applied to people occupying the space or room is safe (e.g., less than a maximum allowable UV dosage).

Further, the disclosure comprises embodiments according to the following clauses:

Clause 1. A sanitizing system comprising:

an ultraviolet (UV) lamp configured to emit UV light into a target space;

an occupancy sensor configured to monitor the target space and generate sensor signals indicative of an occupancy of the target space by at least one person; and a control unit, comprising one or more processors, operably connected to the occupancy sensor and the UV lamp, the control unit configured to receive the sensor signals generated by the occupancy sensor and to modulate an irradiance of the UV light emitted by the UV lamp over time based on the occupancy of the target space.

Clause 2. The sanitizing system of Clause 1, wherein the control unit is configured to analyze historical occupancy data that includes the sensor signals that are generated by the occupancy sensor over a first time period to determine a periodic occupancy trend for the target space, the control unit configured to modulate the irradiance of the UV light emitted by the UV lamp during a second time period based on the periodic occupancy trend, wherein the first time period has a longer duration than the second time period and ends prior to a start of the second time period.

Clause 3. The sanitizing system of Clause 2, wherein the second time period is a day and the first time period is at least a month.

Clause 4. The sanitizing system of Clause 2, wherein the control unit is configured to revise the modulation of the irradiance during the second time period based on the sensor signals generated by the occupancy sensor during the second time period.

Clause 5. The sanitizing system of Clause 2, wherein the control unit is configured to predict, based on the periodic occupancy trend, that the target space will be unoccupied during a time window that is upcoming, and controls the UV lamp to emit the UV light at a full irradiance level at a start of the time window.

Clause 6. The sanitizing system of any of Clauses 1-5, wherein, in response to the sensor signals indicating that the target space is unoccupied, the control unit is configured to operate the UV lamp to emit the UV light at a full irradiance level.

Clause 7. The sanitizing system of Clause 6, wherein the control unit is configured to deactivate the UV lamp to cease emitting the UV light at the full irradiance level, while the target space is unoccupied, after a predetermined time period for disinfection.

Clause 8. The sanitizing system of Clause 6, wherein, in response to the sensor signals indicating that the target space is occupied for a period of time that does not exceed a first threshold time period, the control unit is configured to operate the UV lamp to emit the UV light at the full irradiance level.

Clause 9. The sanitizing system of Clause 5, wherein the UV lamp is configured to emit the UV light at a wavelength range, and the control unit is configured to determine the first threshold time period and the full irradiance level based on the wavelength range of the UV light that is emitted by the UV lamp.

Clause 10. The sanitizing system of any of Clauses 1-9, wherein, in response to the sensor signals indicating that the target space is occupied for a period of time exceeding a first threshold time period, the control unit is configured to control the UV lamp to reduce the irradiance of the UV light to a reduced irradiance level while continuing to emit the UV light into the target space.

Clause 11. The sanitizing system of Clause 10, wherein the first threshold time period is a value within a range from 1 second to 10 seconds.

Clause 12. The sanitizing system of Clause 10, wherein the reduced irradiance level is a first reduced irradiance level, and in response to the sensor signals indicating that the target space is occupied for a period of time exceeding a second threshold time period that is greater than the first threshold time period, the one or more processors are configured to control the UV lamp to reduce the irradiance of the UV light to a second reduced irradiance level while continuing to emit the UV light into the target space, wherein the UV light at the first reduced irradiance level has greater power than the UV light at the second reduced irradiance level.

Clause 13. The sanitizing system of Clause 12, wherein the second threshold time period is a value within a range from 3 seconds to 20 seconds.

Clause 14. The sanitizing system of Clause 10, wherein, in response to the sensor signals indicating that the target space is occupied for a period of time exceeding a second threshold time period that is greater than the first threshold time period, the control unit is configured to deactivate the UV lamp to cease emitting the UV light.

Clause 15. The sanitizing system of Clause 14, wherein the second threshold time period is a value within a range from 10 seconds to 40 seconds.

Clause 16. The sanitizing system of any of Clauses 1-15, wherein the UV lamp and the occupancy sensor are mounted within a room, and the UV light is configured to disinfect one or more components located within the room.

Clause 17. The sanitizing system of Clause 16, wherein the room is within an internal cabin of a vehicle.

Clause 18. The sanitizing system of Clause 16, wherein the room is a lavatory.

Clause 19. The sanitizing system of any of Clauses 1-18, wherein the occupancy sensor is a retro-reflective optical sensor that reflects an energy beam across the target space to detect occupancy based on an interruption in an optical path defined by the energy beam.

Clause 20. The sanitizing system of any of Clauses 1-19, wherein the UV lamp includes a wavelength selective filter configured to block emission of one or more wavelengths of the UV light into the target space.

Clause 21. The sanitizing system of any of Clauses 1-20, wherein the occupancy sensor is separate and spaced apart from the UV lamp.

Clause 22. The sanitizing system of any of Clauses 1-21, wherein UV lamp is configured to emit the UV light at one or more wavelengths between 200 nm and 280 nm.

Clause 23. The sanitizing system of any of Clauses 1-22, wherein the occupancy sensor is a first occupancy sensor and the sensor signals generated by the first occupancy sensor are first sensor signals, wherein the sanitizing system further comprises a second occupancy sensor configured to monitor the target space and generate second sensor signals over time indicative of the occupancy of the target space, wherein the control unit is configured to receive the first and second sensor signals and to determine whether a person is entering or exiting the target space based on the first and second sensor signals.

Clause 24. A method comprising:
emitting ultraviolet (UV) light into a target space;
monitoring the target space via one or more occupancy sensors, the one or more occupancy sensors configured to generate sensor signals indicative of an occupancy of the target space by at least one person;
analyzing the sensor signals via a control unit comprising one or more processors; and
modulating, via the control unit, an irradiance of the UV light emitted into the target space over time based on the occupancy of the target space.

Clause 25. The method of Clause 24, wherein modulating the irradiance of the UV light includes emitting the UV light into the target space at a full irradiance level responsive to determining, via the sensor signals, that the target space is unoccupied.

Clause 26. The method of Clause 24 or 25, wherein modulating the irradiance of the UV light includes emitting the UV light into the target space at a full irradiance level responsive to determining, via the sensor signals, that the target space is occupied for a period of time that does not exceed a first threshold time period.

Clause 27. The method of any of Clauses 24-26, wherein modulating the irradiance of the UV light includes reducing the irradiance of UV light emitted into the target space responsive to determining, via the sensor signals, that the target space is occupied for a period of time that exceeds a first threshold time period.

Clause 28. The method of Clause 27, wherein modulating the irradiance of the UV light includes reducing the irradiance of UV light emitted into the target space a second time, while continuing to emit the UV light into the target space, in response to determining, via the sensor signals, that the target space is occupied for a period of time that exceeds a second threshold time period that is longer than the first threshold time period.

Clause 29. The method of Clause 28, wherein modulating the irradiance of the UV light includes stopping emission of the UV light into the target space, in response to determining, via the sensor signals, that the target space is occupied for a period of time that exceeds a third threshold time period that is longer than the second threshold time period.

Clause 30. A sanitizing system disposed onboard a vehicle, the sanitizing system comprising:
a first ultraviolet (UV) system including a first lamp subset of one or more UV lamps and a first sensor subset of one or more occupancy sensors, the first lamp subset configured to emit UV light into a first target space within the vehicle and the first sensor subset configured to generate first sensor signals indicative of an occupancy of the first target space by at least one person;

a second UV system including a second lamp subset of one or more UV lamps and a second sensor subset of one or more occupancy sensors, the second lamp subset configured to emit UV light into a second target space within the vehicle and the second sensor subset configured to generate second sensor signals indicative of an occupancy of the second target space by at least one person; and a control unit, comprising one or more processors, operably connected to the first UV system and the second UV system, wherein the control unit is configured to (i) receive the first sensor signals generated by the first sensor subset and the second sensor signals generated by the second sensor subset, (ii) modulate an irradiance of the UV light emitted by the first lamp subset over time based on the occupancy of the first target space, and (iii) modulate an irradiance of the UV light emitted by the second lamp subset over time based on the occupancy of the second target space.

Clause 31. The sanitizing system of Clause 30, wherein the first and second target spaces are different areas or rooms within an internal cabin of the vehicle.

Clause 32. The sanitizing system of Clause 30 or 31, wherein the vehicle is a passenger aircraft.

While various spatial and directional terms, such as top, bottom, lower, mid, lateral, horizontal, vertical, front and the like can be used to describe embodiments of the present disclosure, it is understood that such terms are merely used with respect to the orientations shown in the drawings. The orientations can be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described embodiments (and/or aspects thereof) can be used in combination with each other. In addition, many modifications can be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims and the detailed description herein, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and can include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A sanitizing system comprising:
   an ultraviolet (UV) lamp configured to emit UV light into a target space;
   an occupancy sensor configured to monitor the target space and generate sensor signals indicative of an occupancy of the target space by at least one person; and
   a control unit comprising one or more processors operably connected to the occupancy sensor and the UV lamp, the control unit configured to:
     receive the sensor signals generated by the occupancy sensor,
     analyze historical occupancy data that includes the sensor signals that are generated by the occupancy sensor over a first time period to determine a periodic occupancy trend for the target space, and
     modulate an irradiance of the UV light emitted by the UV lamp during a second time period based on the periodic occupancy trend, wherein the first time period has a longer duration than the second time period and ends prior to a start of the second time period.

2. The sanitizing system of claim 1, wherein the second time period is a day and the first time period is at least a month.

3. The sanitizing system of claim 1, wherein the control unit is further configured to revise the modulation of the irradiance during the second time period based on the sensor signals generated by the occupancy sensor during the second time period.

4. The sanitizing system of claim 1, wherein the control unit is configured to predict, based on the periodic occupancy trend, that the target space will be unoccupied during a time window that is upcoming, and controls the UV lamp to emit the UV light at a full irradiance level at a start of the time window.

5. The sanitizing system of claim 1, wherein the UV lamp and the occupancy sensor are mounted within a room, and the UV light is configured to disinfect one or more components located within the room.

6. The sanitizing system of claim 5, wherein the room is within an internal cabin of a vehicle.

7. The sanitizing system of claim 5, wherein the room is a lavatory.

8. The sanitizing system of claim 1, wherein the occupancy sensor is a retro-reflective optical sensor that reflects an energy beam across the target space to detect occupancy based on an interruption in an optical path defined by the energy beam.

9. The sanitizing system of claim 1, wherein the UV lamp includes a wavelength selective filter configured to block emission of one or more wavelengths of the UV light into the target space.

10. The sanitizing system of claim 1, wherein the occupancy sensor is separate and spaced apart from the UV lamp.

11. The sanitizing system of claim 1, wherein the UV lamp is configured to emit the UV light at one or more wavelengths between 200 nm and 280 nm.

12. The sanitizing system of claim 1, wherein the occupancy sensor is a first occupancy sensor and the sensor signals generated by the first occupancy sensor are first sensor signals, wherein the sanitizing system further comprises a second occupancy sensor configured to monitor the target space and generate second sensor signals over time indicative of the occupancy of the target space, wherein the control unit is further configured to receive the first and second sensor signals and to determine whether a person is entering or exiting the target space based on the first and second sensor signals.

13. A method comprising:
emitting ultraviolet (UV) light into a target space;
monitoring the target space via one or more occupancy sensors, the one or more occupancy sensors configured to generate sensor signals indicative of an occupancy of the target space by at least one person;
analyzing the sensor signals via a control unit comprising one or more processors; and
modulating, via the control unit, an irradiance of the UV light emitted into the target space over time based on the occupancy of the target space, wherein modulating the irradiance of the UV light includes:
reducing the irradiance of UV light emitted into the target space responsive to determining, via the sensor signals, that the target space is occupied for a period of time that exceeds a first threshold time period; and
reducing the irradiance of UV light emitted into the target space a second time, while continuing to emit the UV light into the target space, in response to determining, via the sensor signals, that the target space is occupied for a period of time that exceeds a second threshold time period that is longer than the first threshold time period.

14. The method of claim 13, wherein modulating the irradiance of the UV light includes emitting the UV light into the target space at a full irradiance level responsive to determining, via the sensor signals, that the target space is unoccupied.

15. The method of claim 13, wherein modulating the irradiance of the UV light includes emitting the UV light into the target space at a full irradiance level responsive to determining, via the sensor signals, that the target space is occupied for a period of time that does not exceed the first threshold time period.

16. The method of claim 13, wherein modulating the irradiance of the UV light further includes stopping emission of the UV light into the target space, in response to determining, via the sensor signals, that the target space is occupied for a period of time that exceeds a third threshold time period that is longer than the second threshold time period.

17. A sanitizing system comprising:
an ultraviolet (UV) lamp configured to emit UV light into a target space;
an occupancy sensor configured to monitor the target space and generate sensor signals indicative of an occupancy of the target space by at least one person; and
a control unit comprising one or more processors operably connected to the occupancy sensor and the UV lamp, the control unit configured to receive the sensor signals generated by the occupancy sensor and to modulate an irradiance of the UV light emitted by the UV lamp over time based on the occupancy of the target space,
wherein, in response to the sensor signals indicating that the target space is occupied for a period of time exceeding a first threshold time period, the control unit is configured to control the UV lamp to reduce the irradiance of the UV light to a reduced irradiance level while continuing to emit the UV light into the target space, and wherein the first threshold time period is a value within a range from 1 second to 10 seconds.

18. The sanitizing system of claim 17, wherein, in response to the sensor signals indicating that the target space is unoccupied, the control unit is further configured to operate the UV lamp to emit the UV light at a full irradiance level.

19. The sanitizing system of claim 18, wherein the control unit is further configured to deactivate the UV lamp to cease emitting the UV light at the full irradiance level, while the target space is unoccupied, after a predetermined time period for disinfection.

20. The sanitizing system of claim 18, wherein, in response to the sensor signals indicating that the target space is occupied for a period of time that does not exceed a second threshold time period, the control unit is further configured to operate the UV lamp to emit the UV light at the full irradiance level.

21. The sanitizing system of claim 20, wherein the UV lamp is configured to emit the UV light at a wavelength range, and the control unit is further configured to determine the first threshold time period and the full irradiance level based on the wavelength range of the UV light that is emitted by the UV lamp.

22. The sanitizing system of claim 17, wherein the reduced irradiance level is a first reduced irradiance level, and in response to the sensor signals indicating that the target space is occupied for a period of time exceeding a second threshold time period that is greater than the first threshold time period, the control unit is further configured to control the UV lamp to reduce the irradiance of the UV light to a second reduced irradiance level while continuing to emit the UV light into the target space, and wherein the UV light at the first reduced irradiance level has greater power than the UV light at the second reduced irradiance level.

23. The sanitizing system of claim 22, wherein the second threshold time period is a value within a range from 3 seconds to 20 seconds.

24. The sanitizing system of claim 17, wherein, in response to the sensor signals indicating that the target space is occupied for a period of time exceeding a second threshold time period that is greater than the first threshold time period, the control unit is further configured to deactivate the UV lamp to cease emitting the UV light.

25. The sanitizing system of claim 24, wherein the second threshold time period is a value within a range from 10 seconds to 40 seconds.

26. A sanitizing system comprising:
an ultraviolet (UV) lamp configured to emit UV light into a target space;

an occupancy sensor configured to monitor the target space and generate sensor signals indicative of an occupancy of the target space by at least one person; and a control unit comprising one or more processors operably connected to the occupancy sensor and the UV lamp, the control unit configured to receive the sensor signals generated by the occupancy sensor and to modulate an irradiance of the UV light emitted by the UV lamp over time based on the occupancy of the target space, wherein, in response to the sensor signals indicating that the target space is occupied for a period of time exceeding a first threshold time period, the control unit is configured to control the UV lamp to reduce the irradiance of the UV light to a reduced irradiance level while continuing to emit the UV light into the target space, wherein the reduced irradiance level is a first reduced irradiance level, and in response to the sensor signals indicating that the target space is occupied for a period of time exceeding a second threshold time period that is greater than the first threshold time period, the control unit is configured to control the UV lamp to reduce the irradiance of the UV light to a second reduced irradiance level while continuing to emit the UV light into the target space, and wherein the UV light at the first reduced irradiance level has greater power than the UV light at the second reduced irradiance level.

27. The sanitizing system of claim 26, wherein the first threshold time period is a value within a range from 1 second to 10 seconds.

28. The sanitizing system of claim 26, wherein the second threshold time period is a value within a range from 3 seconds to 20 seconds.

29. A sanitizing system comprising:
an ultraviolet (UV) lamp configured to emit UV light into a target space;
an occupancy sensor configured to monitor the target space and generate sensor signals indicative of an occupancy of the target space by at least one person; and
a control unit comprising one or more processors operably connected to the occupancy sensor and the UV lamp, the control unit configured to receive the sensor signals generated by the occupancy sensor and to modulate an irradiance of the UV light emitted by the UV lamp over time based on the occupancy of the target space,
wherein, in response to the sensor signals indicating that the target space is occupied for a period of time exceeding a first threshold time period, the control unit is configured to control the UV lamp to reduce the irradiance of the UV light to a reduced irradiance level while continuing to emit the UV light into the target space, and wherein, in response to the sensor signals indicating that the target space is occupied for a period of time exceeding a second threshold time period that is greater than the first threshold time period, the control unit is configured to deactivate the UV lamp to cease emitting the UV light.

30. The sanitizing system of claim 29, wherein the second threshold time period is a value within a range from 10 seconds to 40 seconds.

31. The sanitizing system of claim 29, wherein the UV lamp and the occupancy sensor are mounted within a room, and the UV light is configured to disinfect one or more components located within the room.

* * * * *